(12) United States Patent
Teather et al.

(10) Patent No.: US 9,809,865 B2
(45) Date of Patent: Nov. 7, 2017

(54) **ANTI-MICROBIAL AGENT FROM *PAENIBACILLUS* SP. AND METHODS AND USES THEREOF**

(71) Applicant: Best Environmental Technologies, Inc., St. Michael (BB)

(72) Inventors: Ronald Teather, Lethbridge (CA); John Baah, Lethbridge (CA); Karim Naghmouchi, Tunis (TN); James Gibbs Watson, Edmonton (CA); Djamel Drider, Villeneuve d'Ascq (FR)

(73) Assignee: Best Environmental Technologies, Inc., St. Michael (BB)

( * ) Notice: Subject to any disclaimer, the term of this patent is extended or adjusted under 35 U.S.C. 154(b) by 0 days.

(21) Appl. No.: 14/642,158

(22) Filed: Mar. 9, 2015

(65) Prior Publication Data
US 2015/0320830 A1 Nov. 12, 2015

Related U.S. Application Data

(63) Continuation-in-part of application No. 13/611,160, filed on Sep. 12, 2012, now abandoned, which is a continuation-in-part of application No. 13/296,063, filed on Nov. 14, 2011, now abandoned, which is a continuation-in-part of application No. PCT/CA2009/001808, filed on Dec. 9, 2009.

(51) Int. Cl.
| | |
|---|---|
| *A23B 4/12* | (2006.01) |
| *A23B 4/24* | (2006.01) |
| *C12R 1/01* | (2006.01) |
| *A61K 35/742* | (2015.01) |
| *A23B 4/22* | (2006.01) |
| *A23L 3/3571* | (2006.01) |
| *A61K 38/12* | (2006.01) |
| *A61K 38/16* | (2006.01) |
| *A61Q 17/00* | (2006.01) |
| *A61K 8/99* | (2017.01) |
| *A61K 35/741* | (2015.01) |
| *C07K 7/62* | (2006.01) |
| *C07K 14/195* | (2006.01) |
| *A23K 10/16* | (2016.01) |
| *A23K 10/18* | (2016.01) |
| *A23K 50/75* | (2016.01) |
| *A23L 33/135* | (2016.01) |

(52) U.S. Cl.
CPC .......... *C12R 1/01* (2013.01); *A23B 4/22* (2013.01); *A23K 10/16* (2016.05); *A23K 10/18* (2016.05); *A23K 50/75* (2016.05); *A23L 3/3571* (2013.01); *A23L 33/135* (2016.08); *A61K 8/99* (2013.01); *A61K 35/741* (2013.01); *A61K 35/742* (2013.01); *A61K 38/12* (2013.01); *A61K 38/164* (2013.01); *A61Q 17/005* (2013.01); *C07K 7/62* (2013.01); *C07K 14/195* (2013.01); *A23V 2002/00* (2013.01)

(58) Field of Classification Search
None
See application file for complete search history.

(56) References Cited

FOREIGN PATENT DOCUMENTS

CN 103146614 A * 6/2013

OTHER PUBLICATIONS

Naghmouchi et al., Colistin A and colistin B among inhibitory substances of Paenibacillus polymyxa JB05-01-1 Arch Microbiol (2012) 194:363-370.*
Piuri et al A novel antimicrobial activity of a Paenibacillus polymyxa strain isolated from regional fermented sausages Letters in Applied Microbiology 1998, 27, 9-13.*
He et al Isolation and Identification of a Paenibacillus polymyxa Strain That Coproduces a Novel Lantibiotic and Polymyxin. Appl. Environ. Microbiol. Jan. 2007 vol. 73 No. 1 168-178.*
Bergen et al., Colistin Methanesulfonate Is an Inactive Prodrug of Colistin against Pseudomonas aeruginosa Antimicrobial Agents and Chemotherapy, Jun. 2006, p. 1953-1958.*
May 14, 2016 IPO Webinar on New Subject Matter Eligibility Guidelines pp. 1-17.*
Office Action dated Sep. 23, 2016 in corresponding Canadian Patent Application No. 2,781,883, 6 pages.
Office Action dated Jan. 25, 2016 in corresponding Canadian Patent Application No. 2,781,883, 5 pages.

* cited by examiner

*Primary Examiner* — Maria Leavitt
(74) *Attorney, Agent, or Firm* — Hovey Williams LLP

(57) ABSTRACT

The present invention provides, in part, a *Paenibacillus* sp. isolate, designated *Paenibacillus polymyxa* JB05-01-1, as well as an anti-microbial agent obtained from the bacterium or cell culture supernatant thereof. Compositions, methods and uses are also provided.

9 Claims, 9 Drawing Sheets

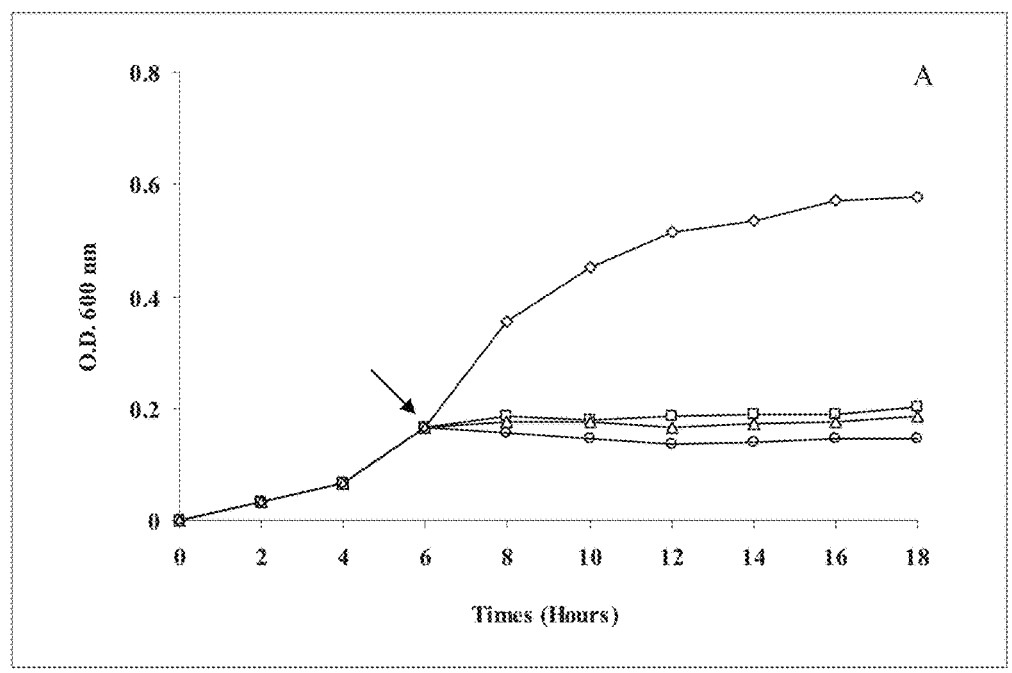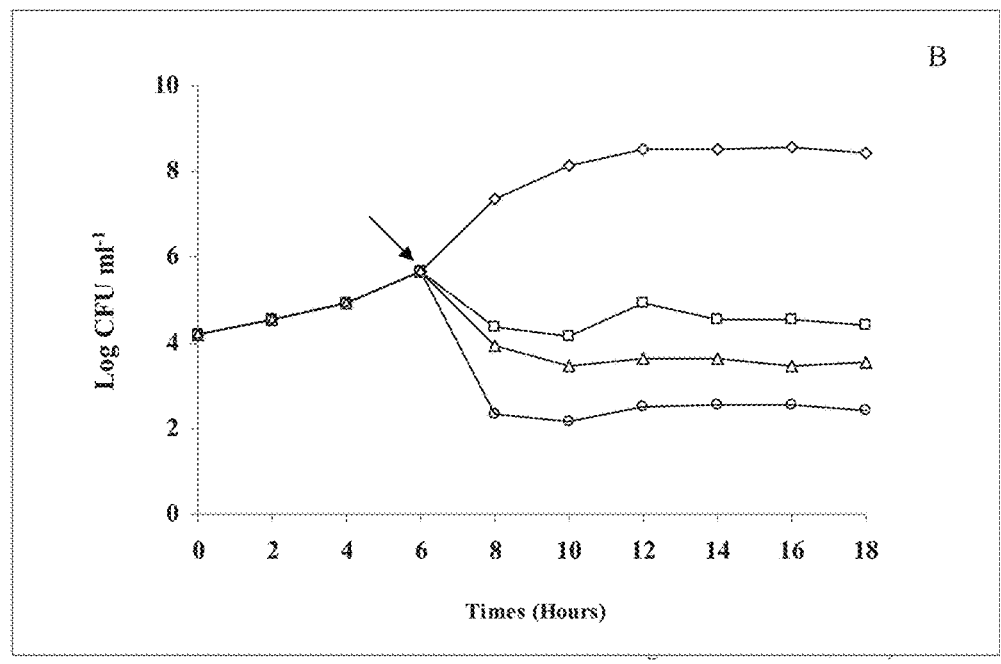
Figure 2

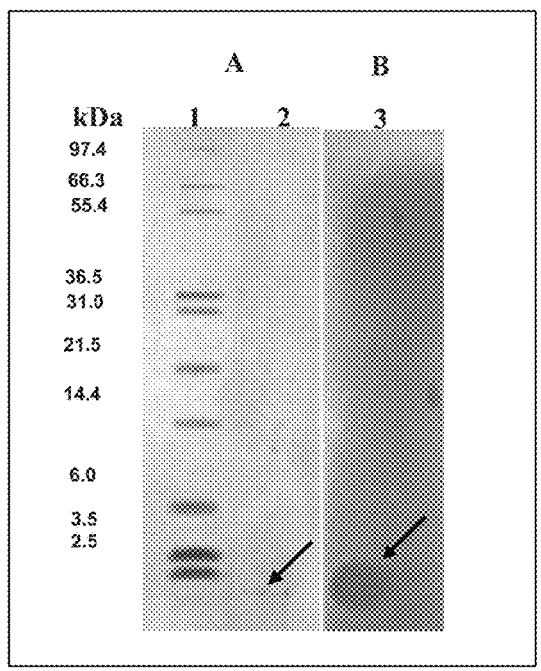

Figure 3

```
   1 agagtttgat cctggctcag aacgaacgct ggcggcgtgc ctaatacatg caagtcgagc
  61 ggggttgatt agaagcttgc ttctaatcaa cctagcggcg gacgggtgag taacacgtag
 121 gcaacctgcc cacaagacag ggataactac cggaaacggt agctaatacc cgatacatcc
 181 ttttcctgca tgggagaagg aggaaagacg gagcaatctg tcacttgtgg atgggcctgc
 241 ggcgcattag ctagttggtg gggtaaaggc ctaccaaggc gacgatgcgt agccgacctg
 301 agagggtgat cggccacact gggactgaga cacggcccag actcctacgg gaggcagcag
 361 tagggaatct tccgcaatgg gcgaaagcct gacggagcaa cgccgcgtga gtgatgaagg
 421 ttttcggatc gtaaagctct gttgccaggg aagaacgtct tgtagagtaa ctgctacaag
 481 agtgacggta cctgagaaga aagccccggc taactacgtg ccagcagccg cggtaatacg
 541 taggggcaa gcgttgtccg gaattattgg gcgtaaagcg cgcgcaggcg gtctttaag
 601 tctggtgttt aatcccgagg ctcaacttcg gtcgcactg gaaactgggg agcttgagtg
 661 cagaagagga gagtggaatt ccacgtgtag cggtgaaatg cgtagatatg tggaggaaca
 721 ccagtggcga aggcgactct ctgggctgta actgacgctg aggcgcgaaa gcgtggggag
 781 caaacaggat tagataccct ggtagtccac gccgtaaacg atgaatgcta ggtgttaggg
 841 gtttcgatac ccttggtgcc gaagttaaca cattaagcat tccgcctggg gagtacggtc
 901 gcaagactga aactcaaagg aattgacggg gacccgcaca agcagtggag tatgtggttt
 961 aattcgaagc aacgcgaaga accttaccag gtcttgacat ccctctgacc ggtctagaga
1021 tagatctttc cttcgggaca gaggagacag gtggtgcatg gttgtcgtca gctcgtgtcg
1081 tgagatgttg ggttaagtcc cgcaacgagc gcaaccctta tgcttagttg ccagcaggtc
1141 aagctgggca ctctaagcag actgccggtg acaaaccgga ggaaggtggg gatgacgtca
1201 aatcatcatg ccccttatga cctgggctac acacgtacta caatggccgg tacaacggga
1261 agcgaaatcg cgaggtggag ccaatcctag aaagccggt ctcagttcgg attgtaggct
1321 gcaactcgcc tacatgaagt cggaattgct agtaatcgcg gatcagcatg ccgcggtgaa
1381 tacgttcccg ggtcttgtac acaccgcccg tcacaccacg agagtttaca cacccgaag
1441 tcggtggggt aacccgc (SEQ ID NO:1)
```

Figure 4

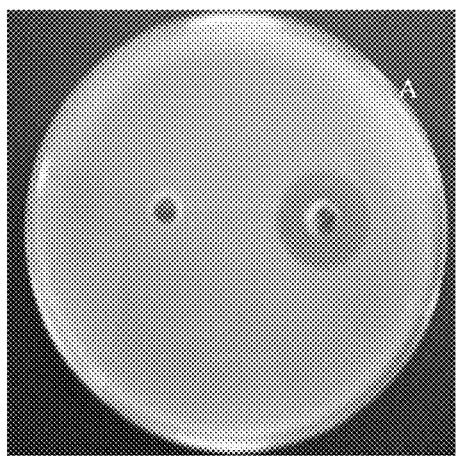
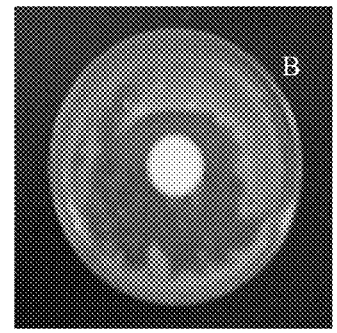
FIGURE 7A                    FIGURE 7B
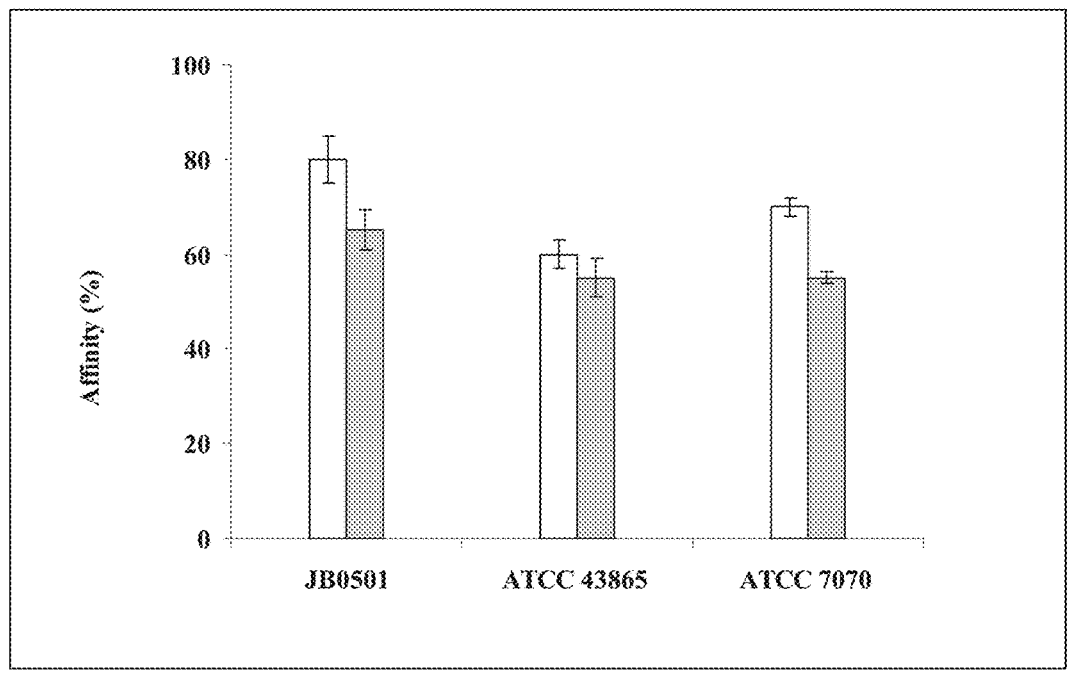
FIGURE 8

SEQUENCE LISTING

```
<160> NUMBER OF SEQ ID NOS: 19

<210> SEQ ID NO 1
<211> LENGTH: 1457
<212> TYPE: DNA
<213> ORGANISM: Paenibacillus polymyxa

<400> SEQUENCE: 1
agagtttgat cctggctcag aacgaacgct ggcggcgtgc ctaatacatg caagtcgagc      60
ggggttgatt agaagcttgc ttctaatcaa cctagcggcg gacgggtgag taacacgtag     120
gcaacctgcc cacaagacag ggataactac cggaaacggt agctaatacc cgatacatcc     180
ttttcctgca tgggagaagg aggaaagacg gagcaatctg tcacttgtgg atgggcctgc     240
ggcgcattag ctagttggtg gggtaaaggc ctaccaaggc gacgatgcgt agccgacctg     300
agagggtgat cggccacact gggactgaga cacggcccag actcctacgg gaggcagcag     360
tagggaatct tccgcaatgg gcgaaagcct gacggagcaa cgccgcgtga gtgatgaagg     420
ttttcggatc gtaaagctct gttgccaggg aagaacgtct tgtagagtaa ctgctacaag     480
agtgacggta cctgagaaga aagccccggc taactacgtg ccagcagccg cggtaatacg     540 taggggcaa gcgttgtccg gaattattgg gcgtaaagcg cgcgcaggcg gctctttaag     600
tctggtgttt aatcccgagg ctcaacttcg ggtcgcactg gaaactgggg agcttgagtg     660
cagaagagga gagtggaatt ccacgtgtag cggtgaaatg cgtagatatg tggaggaaca     720
ccagtggcga aggcgactct ctgggctgta actgacgctg aggcgcgaaa gcgtggggag     780
caaacaggat tagatacct ggtagtccac gccgtaaacg atgaatgcta ggtgttaggg     840
```

```
gtttcgatac ccttggtgcc gaagttaaca cattaagcat tccgcctggg gagtacggtc      900
gcaagactga aactcaaagg aattgacggg acccgcaca agcagtggag tatgtggttt      960
aattcgaagc aacgcgaaga accttaccag gtcttgacat ccctctgacc ggtctagaga     1020
tagatctttc cttcgggaca gaggagacag gtggtgcatg gttgtcgtca gctcgtgtcg     1080
tgagatgttg ggttaagtcc cgcaacgagc gcaaccctta tgcttagttg ccagcaggtc     1140
aagctgggca ctctaagcag actgccggtg acaaaccgga ggaaggtggg gatgacgtca     1200
aatcatcatg ccccttatga cctgggctac acacgtacta caatggccgg tacaacggga     1260
agcgaaatcg cgaggtggag ccaatcctag aaaagccggt ctcagttcgg attgtaggct     1320
gcaactcgcc tacatgaagt cggaattgct agtaatcgcg gatcagcatg ccgcggtgaa     1380
tacgttcccg ggtcttgtac acaccgcccg tcacaccacg agagtttaca cacccgaag      1440 tcggtggggt aacccgc                                                    1457

<210> SEQ ID NO 2
<211> LENGTH: 20
<212> TYPE: DNA
<213> ORGANISM: Artificial Sequence
<220> FEATURE:
<223> OTHER INFORMATION: Primer PEG83_F

<400> SEQUENCE: 2
atgaatgaca tgcagttata                                                   20

<210> SEQ ID NO 3
<211> LENGTH: 20
<212> TYPE: DNA
<213> ORGANISM: Artificial Sequence
<220> FEATURE:
<223> OTHER INFORMATION: Primer PEG83_R

<400> SEQUENCE: 3
ttaggacaaa atgggcttgt                                                   20

<210> SEQ ID NO 4
<211> LENGTH: 20
<212> TYPE: DNA
<213> ORGANISM: Artificial Sequence
<220> FEATURE:
<223> OTHER INFORMATION: Primer PEG1749_F

<400> SEQUENCE: 4
atgagaaacg cactcattca                                                   20

<210> SEQ ID NO 5
<211> LENGTH: 25
<212> TYPE: DNA
<213> ORGANISM: Artificial Sequence
<220> FEATURE:
<223> OTHER INFORMATION: Primer PEG1749_R

<400> SEQUENCE: 5
ctaggaagat gtattatttt tatag                                             25

<210> SEQ ID NO 6
<211> LENGTH: 23
<212> TYPE: DNA
<213> ORGANISM: Artificial Sequence
<220> FEATURE:
<223> OTHER INFORMATION: Primer PEG1750_F

<400> SEQUENCE: 6
```

-continued atgagtaaag atctgcaaat tca                                              23

<210> SEQ ID NO 7
<211> LENGTH: 20
<212> TYPE: DNA
<213> ORGANISM: Artificial Sequence
<220> FEATURE:
<223> OTHER INFORMATION: Primer PEG1750_R

<400> SEQUENCE: 7
ttacagaacc gctgcccagc                                                  20

<210> SEQ ID NO 8
<211> LENGTH: 21
<212> TYPE: DNA
<213> ORGANISM: Artificial Sequence
<220> FEATURE:
<223> OTHER INFORMATION: Primer PEG1962_F

<400> SEQUENCE: 8
atgttctatg cattaacgca t                                                21

<210> SEQ ID NO 9
<211> LENGTH: 24
<212> TYPE: DNA
<213> ORGANISM: Artificial Sequence
<220> FEATURE:
<223> OTHER INFORMATION: Primer PEG1962_R

<400> SEQUENCE: 9
ttattcaaaa agcaattcaa tatc                                             24

<210> SEQ ID NO 10
<211> LENGTH: 20
<212> TYPE: DNA
<213> ORGANISM: Artificial Sequence
<220> FEATURE:
<223> OTHER INFORMATION: PEG1977_F

<400> SEQUENCE: 10
atgcattatg aaggatatga                                                  20

<210> SEQ ID NO 11
<211> LENGTH: 20
<212> TYPE: DNA
<213> ORGANISM: Artificial Sequence
<220> FEATURE:
<223> OTHER INFORMATION: Primer PEG1977_R

<400> SEQUENCE: 11
ttacctcaaa aatgtattca                                                  20

<210> SEQ ID NO 12
<211> LENGTH: 21
<212> TYPE: DNA
<213> ORGANISM: Artificial Sequence
<220> FEATURE:
<223> OTHER INFORMATION: Primer PEG3093_F

<400> SEQUENCE: 12
ttgaaagcct tatttgagaa g                                                21

<210> SEQ ID NO 13
<211> LENGTH: 20
<212> TYPE: DNA

<213> ORGANISM: Artificial Sequence
<220> FEATURE:
<223> OTHER INFORMATION: Primer PEG3093_R

<400> SEQUENCE: 13
tcaagattta tgatgtgcca                    20

<210> SEQ ID NO 14
<211> LENGTH: 23
<212> TYPE: DNA
<213> ORGANISM: Artificial Sequence
<220> FEATURE:
<223> OTHER INFORMATION: Primer PEG5402_F (6913)

<400> SEQUENCE: 14
ttgaaaaagg gcggatggct ctc                23

<210> SEQ ID NO 15
<211> LENGTH: 18
<212> TYPE: DNA
<213> ORGANISM: Artificial Sequence
<220> FEATURE:
<223> OTHER INFORMATION: Primer PEG5402_R (5180)

<400> SEQUENCE: 15
ctagccgtac agccgggc                      18

<210> SEQ ID NO 16
<211> LENGTH: 18
<212> TYPE: DNA
<213> ORGANISM: Artificial Sequence
<220> FEATURE:
<223> OTHER INFORMATION: Primer PEG5403_F (8736)

<400> SEQUENCE: 16
atggaagctg accggcag                      18

<210> SEQ ID NO 17
<211> LENGTH: 19
<212> TYPE: DNA
<213> ORGANISM: Artificial Sequence
<220> FEATURE:
<223> OTHER INFORMATION: Primer PEG5403_R (6910)

<400> SEQUENCE: 17
tcaagtgtac gccacctcc                     19

<210> SEQ ID NO 18
<211> LENGTH: 19
<212> TYPE: DNA
<213> ORGANISM: Artificial Sequence
<220> FEATURE:
<223> OTHER INFORMATION: Primer PEG5404_F (10624)

<400> SEQUENCE: 18
atgtacggag cgctgctgt                     19

<210> SEQ ID NO 19
<211> LENGTH: 19
<212> TYPE: DNA

```
<213> ORGANISM: Artificial Sequence
<220> FEATURE:
<223> OTHER INFORMATION: PEG5404_R (8726)

<400> SEQUENCE: 19
tcagcttcca tgcagtacc                                                  19
```

ANTI-MICROBIAL AGENT FROM *PAENIBACILLUS* SP. AND METHODS AND USES THEREOF

CROSS-REFERENCE TO RELATED APPLICATIONS

The present application is a continuation-in-part of now-abandoned U.S. patent application Ser. No. 13/611,160, filed Sep. 12, 2012, which is a continuation-in-part of now-abandoned U.S. patent application Ser. No. 13/296,063, which was filed on Nov. 14, 2011, the contents of which are both incorporated by reference herein in their entireties. U.S. patent application Ser. No. 13/296,063 is a continuation-in-part of PCT/CA2010/001808, filed on Dec. 9, 2009, and published as WO 2011/069227, the contents of which are incorporated by reference herein in their entireties.

SEQUENCE LISTING

The following application contains a sequence listing in computer readable format (CRF), submitted as a text file in ASCII format entitled "Sequence Listing," created on May 17, 2015, as 6 KB. The content of the CRF is hereby incorporated by reference.

FIELD OF INVENTION

The invention is in the field of anti-microbial agents. More specifically, the invention relates to anti-microbial agents derived from *Paenibacillus*.

BACKGROUND OF THE INVENTION

In response to the increasing prevalence of antibiotic resistance in pathogenic bacteria, the pharmacokinetic properties and safety profiles of many novel antimicrobial peptides have been investigated. Bacteriocins are natural proteinaceous antimicrobial compounds produced by bacteria and active against taxonomically related bacteria (Klaenhammer, 1993). Species that produce bacteriocins have been studied extensively in the hope of finding safe and efficient means of inhibiting the growth of pathogenic bacteria, especially in foods (Cleveland et al. 2001). Bacteriocins produced by Gram-positive staining bacteria, such as lactic acid bacteria, have become a focus of interest as alternatives to conventional antibiotics (Nes et al. 1996). Nisin, the first bacteriocin ever isolated and now widely used as a food additive, was approved by the World Health Organization for use as a food preservative in 1973. This peptide is generally inactive against Gram-negative staining bacteria, imposing a limitation on its effectiveness when major food-borne pathogens such as *Escherichia coli, Salmonella* and *Yersinia* are involved (Du and Shen 1999; Zheng et al. 1999). Davies et al. (1998) reported that nisin produced by *Lactococcus lactis* was thermostable and remained active after treatment at 121° C. for 15 min at pH 3. Nisin is about 4.4 kDa and is stabilized by disulfide bonds.

Polymyxins, a class of antimicrobial agents, are synthesized by a non-ribosomal process. The peptide-synthase directed condensation reactions by which polymyxins are formed in the cell cytoplasm have been reviewed (Marahiel et al. 1997) and their biosynthesis in a cell-free enzyme system reported (Komura et al. 1985).

Many species within the genus *Paenibacillus* produce variants of polymyxins, which are generally composed of a cyclic decapeptide with a terminal fatty acid moiety (Martin et al. 2003). Five chemically distinct compounds, polymyxins A to E, differing in amino acid and fatty acid composition have been identified to date. Martin et al. (2003) reported that mattacin activity (800 AU ml$^{-1}$) produced by *P. kobensis* M was maximal at 12 h of fermentation. Martin et al. (2003) also reported that mattacin and polymyxin B inhibited all Gram-negative staining species tested including *E. coli* O157:H7, *Salmonella enterica* serovar Rubislaw and *Vibrio parahemeolyticus* G1-166 but both failed to inhibit strains of *Listeria* and *Bacillus*.

DeCrescenzo et al. (2007) isolated a new *Paenibacillus* species (*P. amylolyticus* C27) that produces polymyxins E1 and E2 (colistin A and B). The new antimicrobial peptides were reported to be effective against Gram-negative staining bacteria such as *E. coli, Pseudomonas, Salmonella*, and *Shigella*. DeCrescenzo et al. (2007) also reported that polymyxin E produced by *P. amylolyticus* C27 inhibited Gram-positive staining bacteria such as *Staphylococus aureus* ATCC 6538, *Enterococcus faecalis* ATCC 19433 and *Streptococcus pyogenes* ATCC 19165.

Zengguo et al. (2007) reported the co-production of polymyxin and lantibiotic by natural isolates of *P. polymyxa*. The two antimicrobial peptides were reported to display potent activity against many Gram-negative staining bacteria, including *E. coli, Pseudomonas aeruginosa* and *Acinetobacter baumannii*, and against Gram-positive food-borne pathogenic bacteria. Zengguo et al. (2007) also reported that polymyxin produced by *P. polymyxa* OSY-DF is stable from pH 2.0 to 9.0 and retained its activity after a short autoclaving.

Svetoch et al. (2005) reported the isolation of a new class IIa bacteriocin from *P. polymyxa* NRRL-B-30509, which has been used for the control of *Campylobacter* in poultry.

Among antimicrobial substances produced by *Bacillus polymyxa* are polymyxins, which are cyclic peptides with a long hydrophobic tail. Colistin is a polymyxin antibiotic discovered in the late 1940s for the treatment of Gram-negative infections. After several years of clinical use, colistin was associated with significant nephrotoxicity and neurotoxicty (Lim et al. 2010), rendering its use questionable. Colistin has a bactericidal effect against Gram-negative bacteria and acts as a detergent-like molecule (Landman et al. 2008). Recently, its application has returned as the last resort against multidrug-resistant organisms including *Pseudomonas aeruginosa, Acinetobacter baumannii*, and *Klebsiella pneumoniae* (Falagas and Kasiakou 2005).

The need for antibiotics with activity against these multidrug-resistant Gram-negative pathogens is urgent and in the absence of viable alternatives, clinicians now recommend colistin treatment when confronted with some multi-drug resistant bacterial infections (Lim et al. 2010). This has led to the development of less toxic colistin molecules (Jian Li et al. 2004; Falagas et al., 2006). Colistin formulations available for clinical uses are colistin sulfate (for topical use) and colistin methane sulfonate for parenteral and aerosol therapy (Jian Li et al. 2006).

The coproduction of polymyxin E1 and a lantibiotic has been reported for *P. polymyxa* OSY-DF; a strain isolated from food (He et al. 2007). Polymyxin E1 was active against Gram-negative bacteria, whilst paenibacillin, a proteinaceous compound, exhibited activity against Gram-positive bacteria (He et al. 2007 & 2008). *P. kobensis* M isolated from soil produced mattacin (polymixin M) (Nathaniel et al. 2003) and *Bacillus* sp. strain B-60 produced various inhibitory molecules named sattabacin, hydroxysattabacin, sattazolin and methylsattazolin, with antiviral activity against herpes simplex viruses types 1 and 2 (HSV1 and HSV2)

(Lampis et al. 1995). Strains of *P. polymyxa* have been isolated from different ecological niches including food matrices such as butternut squash, potatoes, rice, and wheat flour (Fangio et al. 2010).

Usually, *E. coli* is regarded as an inoffensive and common bacterium of the gastrointestinal tract of ruminants. The emergence of the enterohemorrhagic strain O157:H7 has become a major public concern worldwide. Indeed this pathogen is able to produce potent endotoxins with severe damage to the lining of the intestine, in particular in humans, allowing the strain to invade the body and infect organs such as the kidneys, sometimes with fatal consequences.

Spore-forming species such as *Paenibacillus* or other probiotic bacteria are known in the art. Andersson et al. (1997) showed that *Bacillus cereus* produced spores able to adhere to Caco-2 cell monolayers and to germinate in an environment similar to that of the small intestine and noted that the hydrophobicity of the spore is a contributing factor to adhesion. Angioi et al. (1995) evaluated the capacity of *Bacillus subtilis* strains to colonise the surface of Caco-2 cells, testing the bacteria both in the spore state and following stimulation of germination by exposure to low pH (as under gastric conditions) or to high temperatures. The degree of adhesion was found to vary in relation to the different physiological phases of the bacterial cells. Doyle et al. (1984) showed that spores or cells from several *Bacillus* species displayed a strong affinity for hexadecane and other hydrophobic solvents. Treatment of *Bacillus* spore suspensions with strong denaturants promoted their adherence to hexadecane (Koshikawa et al. 1989).

SUMMARY OF THE INVENTION

The present invention provides, in part, an isolated *Paenibacillus* sp. bacterium comprising SEQ ID NO: 1.

In alternative embodiments, the invention provides an isolated *Paenibacillus polymyxa* (Strain JB05-01-1) bacterium deposited at the ATCC®) under the terms of the Budapest Treaty and designated Accession Number PTA-10436, or a strain comprising the identifying characteristics thereof. The bacterium may be isolated from a direct-fed microbial product. For example, JB05-01-1 was found while examining a mixed culture preparation of RE3™.

The bacterium may include an anti-microbial activity, such as an anti-bacterial activity. The anti-bacterial activity may include inhibiting the growth of a Gram-negative staining bacterium, such as one or more of *Escherichia* sp. (e.g., *Escherichia coli* such as *Escherichia coli* RR1, *Escherichia coli* TB1, or *Escherichia coli* O157:H7), *Pantoea* sp. (e.g., *Pantoea agglomerans* BC1), *Pseudomonas* sp. (e.g., *Pseudomonas fluorescens* R73), *Butyrivibrio* sp. (e.g., *Butyrivibrio fibrisolvens* OR85), *Fibrobacter* sp. (e.g., *Fibrobacter succinogenes*), *Salmonella* sp. (e.g., *Salmonella enteritidis* or *Salmonella typhi*), *Shigella* sp. (e.g., *Shigella dysenteriae*), *Helicobacter* sp. (e.g., *Helicobacter pylori*), or *Campylobacter* sp (e.g., *Campylobacter jejuni*).

The anti-bacterial activity may include inhibiting the growth of a Gram-negative staining bacterium, such as one or more of *Escherichia coli* RR1, *Escherichia coli* TB1, and *Escherichia coli* O157:H7, *Pantoea agglomerans* BC1, *Pseudomonas fluorescens* R73, *Butyrivibrio fibrisolvens* OR85, *Fibrobacter succinogenes* and *Pseudomonas aeruginosa*.

In alternative embodiments, the bacterium may not inhibit the growth of a Gram-positive staining bacterium, such as one or more of a *Listeria innocua*, *Listeria monocytogenes*, *Pediococcus acidilactici*, *Paenibacillus polymyxa*, *Paenibacillus macerans*, *Bacillus lecheniformis*, *Bacillus subtilis*, *Bacillus circulans* 9E2, *Streptococcus bovis*, *Enterococcus mundtii*, *Staphylococcus aureus*, or *Lactococcus lactis*.

In alternative embodiments, the anti-microbial activity may be sensitive to an enzyme selected from the group consisting of one or more of proteinase K, trypsin, chymotrypsin or lipase; or may be sensitive to sodium dodecyl sulphate (SDS) or urea; or may be sensitive to a temperature in excess of about 90° C. for about 30 minutes; or may be sensitive to a temperature of about 100° C. for about 10 minutes; or may be insensitive to a temperature upto about 80° C. for about 30 minutes; or may be sensitive to acetonitrile and hexane; or may be insensitive to an organic solvent selected from the group consisting of chloroform, propanol, methanol, ethanol and toluene; or may be insensitive to pH, for example, pH ranging from about 2 to about 9.

In alternative embodiments, the invention provides a cell culture including a bacterium as described herein. The cell culture may be a starter culture.

In alternative embodiments, the invention provides a cell culture supernatant derived from growing a bacterium as described herein in a cell culture medium. The supernatant may include an anti-microbial activity, such as an anti-bacterial activity.

In alternative embodiments, the invention provides an anti-microbial agent isolated from a bacterium, cell culture, or cell culture supernatant as described herein. The anti-microbial agent may include a peptide, such as a lipopeptide. The anti-microbial agent may include a molecular weight between about 1000 daltons to about 2500 daltons. The anti-microbial agent may be a polymyxin. The anti-microbial agent may be colistin A and/or colistin B.

In alternative embodiments, the invention provides a bacterium, cell culture, cell culture supernatant, or anti-microbial agent as described herein.

In alternative embodiments, the invention provides a pharmaceutical, veterinary, cosmetic or hygiene composition including a bacterium, cell culture, cell culture supernatant, or anti-microbial agent as described herein and a suitable carrier.

In alternative embodiments, the invention provides a food or feed additive comprising a bacterium, cell culture, cell culture supernatant, or anti-microbial agent as described herein.

In alternative embodiments, the invention provides a packaging material comprising a bacterium, cell culture, cell culture supernatant, or anti-microbial agent as described herein.

In alternative embodiments, the invention provides a kit comprising a bacterium, cell culture, cell culture supernatant, or anti-microbial agent as described herein together with instructions for use in inhibiting growth of a microorganism.

In alternative embodiments, the invention provides a method of producing an anti-microbial agent, by providing a live *Paenibacillus* sp. bacterium comprising SEQ ID NO: 1; and culturing the live *Paenibacillus* sp. bacterium in a cell culture medium, under conditions suitable for production of the anti-microbial agent.

In alternative embodiments, the invention provides a method of producing an anti-microbial agent, by providing a live *Paenibacillus polymyxa* (Strain JB05-01-1) bacterium or a strain comprising the identifying characteristics thereof; and culturing the live *Paenibacillus polymyxa* (Strain JB05-01-1) bacterium or a strain comprising the identifying characteristics thereof in a cell culture medium, under conditions suitable for production of the anti-microbial agent.

The methods may further include isolating the anti-microbial agent from the bacterium. The culturing may be performed under conditions suitable for secretion of the anti-microbial agent into the cell culture medium. The methods may further include separating the bacterium from the cell culture medium to provide a cell culture supernatant comprising the anti-microbial agent. The methods may further include isolating the anti-microbial agent from the cell culture supernatant.

In alternative embodiments, the invention provides an anti-microbial agent produced by the methods as described herein. The anti-microbial agent may include a peptide, such as a lipopeptide. The anti-microbial agent may include a molecular weight between about 1000 daltons to about 2500 daltons. The anti-microbial agent may be a polymyxin. The anti-microbial agent may be colistin A and/or colistin B.

The anti-microbial agent may include an anti-microbial activity selected from one or more of: sensitivity to proteinase K, trypsin, chymotrypsin and lipase, sodium dodecyl sulphate (SDS), urea, acetonitrile, or hexane; insensitivity to chloroform, propanol, methanol, ethanol or toluene; insensitivity to pH; sensitivity to a temperature in excess of about 90° C. for about 30 minutes; sensitivity to a temperature of about 100° C. for about 10 minutes; insensitivity to a temperature upto about 80° C. for about 30 minutes; inhibition of growth of a Gram-negative staining bacterium; or no inhibition of growth of a Gram-positive staining bacterium.

In alternative embodiments, the invention provides a method of inhibiting the growth of a microorganism in a subject or substance in need thereof by administering or applying an effective amount of the bacterium, cell culture, cell culture supernatant or anti-microbial agent, as described herein, to the subject or substance. The inhibition of growth may be selective.

The microorganism may be a bacterium, such as a Gram-negative staining bacterium, such as one or more of one or more of *Escherichia* sp. (e.g., *Escherichia coli* such as *Escherichia coli* RR1, *Escherichia coli* TB1, or *Escherichia coli* O157:H7), *Pantoea* sp. (e.g., *Pantoea agglomerans* BC1), *Pseudomonas* sp. (e.g., *Pseudomonas fluorescens* R73 or *Pseudomonas aeruginosa*), *Butyrivibrio* sp. (e.g., *Butyrivibrio fibrisolvens* OR85), *Fibrobacter* sp. (e.g., *Fibrobacter succinogenes*), *Salmonella* sp. (e.g., *Salmonella enteritidis* or *Salmonella typhi*), *Shigella* sp. (e.g., *Shigella dysenteriae*), *Helicobacter* sp. (e.g., *Helicobacter pylori*), or *Campylobacter* sp (e.g., *Campylobacter jejuni*).

The Gram-negative staining bacterium, may be one or more of *Escherichia coli* RR1, *Escherichia coli* TB1, and *Escherichia coli* O157:H7, *Pantoea agglomerans* BC1, *Pseudomonas fluorescens* R73, *Butyrivibrio fibrisolvens* OR85, *Fibrobacter succinogenes* and *Pseudomonas aeruginosa*.

The bacterium may be a pathogenic bacterium, such as a food-borne pathogenic bacterium. The microorganism may be a food-borne pathogenic micro-organism or a food-spoilage micro-organism.

The subject may be an animal, such as a human, a pet, or an agricultural animal (e.g., cow, horse, pig, sheep, goat, chicken, turkey, duck, goose, fish, or crustacean). The substance may be a cosmetic, hygiene, feed or food product (e.g., dairy or meat product) or packaging material thereof.

In alternative embodiments, the invention provides an isolated nucleic acid molecule including SEQ ID NO: 1.

In alternative embodiments, the invention provides the use of an effective amount of a bacterium, cell culture, cell culture supernatant or anti-microbial agent, as described herein for inhibiting the growth of a microorganism in a subject or substance in need thereof.

In alternative embodiments, there is provided a method of inhibiting growth of a Gram-negative staining bacterium in a subject or substance in need thereof, the method comprising administering or applying an effective amount of an anti-microbial composition to the subject or substance, wherein the anti-microbial composition comprises: (a) an isolated *Paenibacillus polymyxa* bacterium which has a 16S ribosomal RNA (16SrRNA) gene containing a DNA comprising the base sequence of SEQ ID NO: 1; (b) an isolated *Paenibacillus polymyxa* bacterium deposited at the ATCC® under the terms of the Budapest Treaty and designated Accession Number PTA-10436; (c) a cell culture comprising the *Paenibacillus polymyxa* bacterium; (d) a cell culture supernatant derived from growing the *Paenibacillus polymyxa* bacterium in a cell culture medium; or (e) an anti-microbial agent isolated from the *Paenibacillus polymyxa* bacterium, the cell culture or the cell culture supernatant.

In alternative embodiments, there is provided a method of producing an anti-microbial agent comprising growing or culturing an isolated *Paenibacillus polymyxa* bacterium which has a 16S ribosomal RNA (16SrRNA) gene containing a DNA comprising the base sequence of SEQ ID NO: 1, or an isolated *Paenibacillus polymyxa* bacterium deposited at the ATCC® under the terms of the Budapest Treaty and designated Accession Number PTA-10436, in a cell culture medium to produce a cell culture supernatant comprising the anti-microbial agent.

In alternative embodiments, there is provided a method of producing an anti-microbial agent comprising growing or culturing an isolated *Paenibacillus polymyxa* bacterium which has a 16S ribosomal RNA (16SrRNA) gene containing a DNA comprising the base sequence of SEQ ID NO: 1, or an isolated *Paenibacillus polymyxa* bacterium deposited at the ATCC® under the terms of the Budapest Treaty and designated Accession Number PTA-10436, in a cell culture medium to produce a cell culture comprising the anti-microbial agent.

In alternative embodiments, there is provided a method of reducing mortality or morbidity of an animal comprising administering an effective amount of an anti-microbial composition to the animal, wherein the anti-microbial composition comprises: (a) an isolated *Paenibacillus polymyxa* bacterium which has a 16S ribosomal RNA (16SrRNA) gene containing a DNA comprising the base sequence of SEQ ID NO: 1; (b) an isolated *Paenibacillus polymyxa* bacterium deposited at the ATCC® under the terms of the Budapest Treaty and designated Accession Number PTA-10436; (c) a cell culture comprising the *Paenibacillus polymyxa* bacterium; (d) a cell culture supernatant derived from growing the *Paenibacillus polymyxa* bacterium in a cell culture medium; or (e) an anti-microbial agent isolated from the *Paenibacillus polymyxa* bacterium, the cell culture or the cell culture supernatant.

In alternative embodiments, there is provided a method of identifying a bacterium useful in producing an antimicrobial agent; a bacterium useful for inhibiting growth of a Gram-negative staining bacterium in a subject or substance in need thereof; or a bacterium useful in reducing mortality or morbidity of an animal. The method may comprise assessing active mixed cultures for the presence of a bacterium comprising a 16S ribosomal RNA (16SrRNA) gene containing a DNA comprising the base sequence of SEQ ID NO: 1; isolating the bacterium that comprises said sequence, and culturing the bacterium as a pure culture. The active mixed culture may be a direct-fed microbial mixed culture. The method may further comprise identifying cultures using the phenotypic or genetic traits of JB05-01-1 disclosed herein.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 2 is a pair of graphs showing the antimicrobial activity against *E. coli* RR1. DiVerent amounts of crude *P. polymyxa* culture supernatant (1 mg/ml) containing antimicrobial substance(s) "JB05-01-1" at 0 (open diamond), 32 (open square), and 96 (open triangle) AU/ml or polymyxin B (0.1 µg/ml) (open circle) were added to exponentially growing culture of *Escherichia coli* RR1 in tryptic soy broth at 30° C., wherein graph A is optical density at 600 nm and graph B is viable cell counts (CFU, colony forming unit). Arrows show crude antimicrobials peptides addition.

FIG. 3 is a photograph showing SDS-PAGE profiles of partially purified antimicrobial substance produced by *Paenibacillus polymyxa* JB05-01-1, wherein the gel in part A was stained with Coomassie Brilliant Blue staining R-250 and the gel in part B was recovered with TSBA pre-overlaid with *E. coli* RR1. Lane 1 contains the molecular weight markers (in KD); Lane 2 contains partly purified antimicrobial substance JB05-01-1. Arrows in gel of parts A and B show a band and a zone of inhibition, respectively.

FIG. 4 is a partial sequence of *P. polymyxa* JB05-01-1 16S rRNA gene (GenBank Accession Number GQ184435; SEQ ID NO: 1).

FIG. 7A is an agar diffusion test showing inhibition of *E. coli* ATCC 25922 by supernatant of 20 h culture of *Paenibacillius polymyxa* JB05-01-1 (right); left=negative control (Tryptic soy broth)

FIG. 7B is a paper disc spot test showing inhibition of *E. coli* ATCC 25922 by *P. polymyxa* JB05-01-1.

FIG. 8 shows the affinity of *P. polymyxa* JB05-01-1, *P. polymyxa* ATCC 43865 and *P. polymyxa* ATCC 7070 strains for hexadecane (White) and decane (grey). Values presented are the means of three independent measurements.

DETAILED DESCRIPTION

Figure 1:
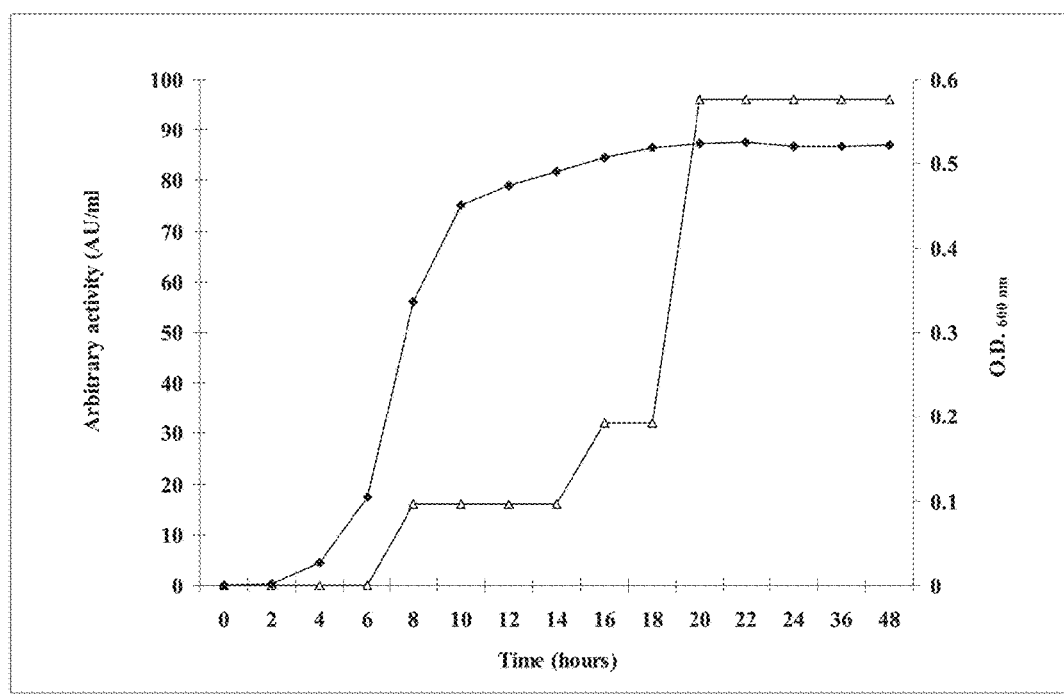
FIG. 1 is a graph showing Kinetics of *P. polymyxa* JB05-01-1 growth and production of "JB05-01-1" during stirred batch culture in Luria-Bertani broth at 30° C. Filled diamond is culture optical density; open triangle is inhibitory activity expressed as AU/ml, determined by microdilution assay

The present invention provides, in part, a *Paenibacillus* sp. isolate, designated *Paenibacillus polymyxa* JB05-01-1 (deposited on Oct. 21, 2009, with the American Type Culture Collection (ATCC®) under the terms of the Budapest Treaty and assigned Accession Number PTA-10436) obtained from an animal feed additive and identified by amplification and sequencing of the 16S rRNA gene. Characterization of the physical properties and anti-microbial activities of a substance secreted into the culture supernatant of a *Paenibacillus polymyxa* JB05-01-1 cell culture resulted in the identification of at least one anti-microbial agent.

Anti-Microbial Agents

An "anti-microbial agent," as used herein, refers to an agent that exhibits one or more "anti-microbial activity" i.e., any activity that inhibits the growth of a micro-organism. By "inhibit," "inhibition" or "inhibiting" is meant to destroy, prevent, control, decrease, slow or otherwise interfere with the growth or survival of a micro-organism by at least about 10% to at least about 100%, or any value therebetween for example about 10%, 15%, 20%, 25%, 30%, 35%, 40%, 45%, 50%, 55%, 60%, 65%, 70%, 75%, 80%, 85%, 90%, 95%, 99%, or 100% when compared to the growth or survival of the micro-organism in the absence of the anti-microbial agent. In alternative embodiments, by "inhibit" "inhibition" or "inhibiting" is meant to destroy, prevent, control, decrease, slow or otherwise interfere with the growth or survival of a micro-organism by at least about 1-fold or more, for example, about 1.5-fold to about 100-fold, or any value therebetween for example about 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95-fold when compared to the growth or survival of the micro-organism in the absence of the anti-microbial agent. In alternative embodiments, the "inhibition" may be more than 100-fold. In alternative embodiments, the "inhibition" may be substantially complete inhibition of growth i.e., the growth rate may be reduced to about zero in the presence of the anti-microbial agent, and the anti-microbial agent may cause death of a micro-organism, when compared to the growth or survival of the micro-organism in the absence of the anti-microbial agent. Accordingly, an anti-microbial agent may be microbicidal or may be microbistatic.

In some embodiments, the anti-microbial agent may be an anti-bacterial agent i.e., an agent that exhibits one or more "anti-bacterial activity" i.e., any activity that inhibits the growth of a bacterium. In alternative embodiments, the anti-bacterial agent may be bactericidal or bacteriostatic.

In some embodiments, an anti-bacterial agent according to the invention may selectively inhibit the growth of a Gram-negative staining bacterium.

By "selectively inhibit" "selective inhibition" or "selectively inhibiting" is meant to destroy, prevent, control, decrease, slow or otherwise interfere with the growth or survival of a Gram-negative staining bacterium by at least about 10% to at least about 100%, or any value therebetween for example about 10%, 15%, 20%, 25%, 30%, 35%, 40%, 45%, 50%, 55%, 60%, 65%, 70%, 75%, 80%, 85%, 90%, 95%, 99%, or 100% when compared to the growth or survival of a Gram-positive staining bacterium. In alternative embodiments, by "selectively inhibit" "selective inhibition" or "selectively inhibiting" is meant to destroy, prevent, control, decrease, slow or otherwise interfere with the growth or survival of a Gram-negative staining bacterium by at least about 1-fold or more, for example, about 1.5-fold to about 100-fold, or any value therebetween for example about 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95-fold when compared to the growth or survival of a Gram-positive staining bacterium. In alternative embodiments, the "selective inhibition" may be more than 100-fold. In alternative embodiments, the "selective inhibition" may be substantially complete inhibition of growth of a Gram-negative staining bacterium i.e., the growth rate could be reduced to about zero and the antibacterial agent may cause death of a Gram-negative staining bacterium when compared to the growth or survival of Gram-positive staining bacterium.

Gram-negative staining bacteria include without limitation *Escherichia* sp., *Pantoea* sp., *Pseudomonas* sp., *Salmonella* sp., *Shigella* sp., *Pseudomonas* sp., *Helicobacter* sp., *Butyrivibrio* sp., *Fibrobacter* sp. or *Campylobacter* sp. Examples of Gram-negative staining bacteria species include without limitation *Escherichia coli* (e.g., *Escherichia coli* RR1, *Escherichia coli* TB1, *Escherichia coli* O157:H7), *Pantoea agglomerans*, *Pseudomonas fluorescens*, *Pseudomonas aeruginosa*, *Salmonella enteritidis*, *Salmonella typhi*, *Shigella dysenteriae*, *Helicobacter pylori*, *Butyrivibrio fibrisolvens*, *Fibrobacter succinogenes* or *Campylobacter jejuni*.

In alternative embodiments, an anti-microbial agent according to the invention does not substantially inhibit the growth of Gram-positive staining bacteria, such as one or more of *Listeria innocua*, *Listeria monocytogenes*, *Pediococcus acidilactici*, *Paenibacillus polymyxa*, *Paenibacillus macerans*, *Bacillus lecheniformis*, *Bacillus subtilis*, *Bacillus circulans* 9E2, *Streptococcus bovis*, *Enterococcus mundtii*, *Staphylococcus aureus*, or *Lactococcus lactis*.

In some embodiments, an anti-microbial agent according to the invention may be sensitive or insensitive to various treatments. By "sensitive" or "sensitivity" is meant loss or reduction of anti-microbial activity by at least about 10% to at least about 100%, or any value therebetween for example about 10%, 15%, 20%, 25%, 30%, 35%, 40%, 45%, 50%, 55%, 60%, 65%, 70%, 75%, 80%, 85%, 90%, 95%, 99%, or 100% when an anti-microbial agent is subjected to a particular treatment, when compared to anti-microbial activity in the absence of the treatment. In alternative embodiments, by "sensitive" or "sensitivity" is meant loss or reduction of anti-microbial activity by at least about 1-fold or more, for example, about 1.5-fold to about 100-fold, or any value therebetween for example about 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95-fold when an anti-microbial agent is subjected to a particular treatment, when compared to anti-microbial activity in the absence of the treatment. In alternative embodiments, the "sensitivity" may include loss or reduction of anti-microbial activity of more than 100-fold.

It is to be understood that sensitivity may vary with the time of treatment. In alternative embodiments, the time of treatment may range from a few minutes to many hours. For example, the time of treatment may be about 5 minutes to over 25 hours, such as 5, 10, 15, 20, 25, 30, 35, 40, 45, 50, or 55 minutes or any value therebetween, or such as 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0 hours, or any value therebetween. Anti-microbial activity may be tested by standard methods such as agar diffusion tests and micro-dilution assay as described herein, or by other standard methods such as disk diffusion, agar dilution, or through the use of automated instrumental testing systems (see, for example, Manual of Clinical Microbiology. 1995. P. M. Murray (ed). ASM Press, Washington, D.C.).

By "insensitive" or "insensitivity" is meant no substantial observable effect or sensitivity when an anti-microbial agent is subjected to a particular treatment, when compared to anti-microbial activity in the absence of the treatment. In alternative embodiments, by "insensitive" or "insensitivity" is meant an observable effect of less than about 10%, for example about 0%, 1%, 2%, 3%, 4%, 5%, 6%, 7%, 8%, or 9% when an anti-microbial agent is subjected to a particular treatment, when compared to anti-microbial activity in the absence of the treatment.

In some embodiments, an anti-microbial agent according to the invention may be sensitive to treatment with proteases such as proteinase K, trypsin, chymotrypsin or with a lipase.

In some embodiments, an anti-microbial agent according to the invention may be sensitive to treatment with surfactants such as sodium dodecyl sulphate (SDS), chaotropics agents such as urea, or solvents such as acetonitrile or hexane.

In some embodiments, an anti-microbial agent according to the invention may be insensitive to an organic solvent such as chloroform, propanol, methanol, ethanol or toluene.

In some embodiments, an anti-microbial agent according to the invention may be insensitive to pH, for example, pH ranging from about 2 to about 9.

In some embodiments, an anti-microbial agent according to the invention may be sensitive to a temperature in excess of about 80° C. In some embodiments, an anti-microbial agent according to the invention may be sensitive to a temperature in excess of about 90° C. Accordingly, in some embodiments, an anti-microbial agent according to the invention may be sensitive to a temperature in excess of about 90° C. when exposed for at least about 30 minutes. In alternative embodiments, an anti-microbial agent according to the invention may be sensitive to a temperature of about 100° C. when exposed for at least about 10 minutes.

In some embodiments, an anti-microbial agent according to the invention may be insensitive to a temperature up to about 80° C. when exposed for about 30 minutes.

In particular embodiments, sensitivity of an anti-microbial agent according to the invention may include: the loss (about 100%) of anti-microbial activity after treatment of a composition including the anti-microbial agent with proteinase K for 10 minutes at 100° C.; the reduction of anti-microbial activity to about 83% or about 75% by trypsin and chymotrypsin, respectively, or to about 62% by lipase; the reduction of anti-microbial activity to about 66% after SDS treatment and about 58% after Urea treatment.

In some embodiments, the molecular weight of an anti-microbial agent according to the invention may be about 1,000 Da to about 2,500 Da. In some embodiments, an anti-microbial agent according to the invention may include more than one molecule having a molecular weight in the range of about 1,000 Da to about 2,500 Da. The agent may be a peptide, for example, a lipopeptide.

In some embodiments, an anti-microbial agent according to the invention may be a peptidic compound including for example a nonproteinaceous amino acid, such as a D-amino acid or a hydroxy acid and/or may be modified for example by N methylation, acylation, glycosylation, or heterocyclic ring formation.

In some embodiments, an anti-microbial agent according to the invention may be a polymyxin. By "polymyxin" is meant a peptide having anti-microbial activity. In general, the structure of a polymyxin may include a cyclic peptide e.g., a cyclic decapeptide, with a terminal fatty acid moiety, that is capable of inhibiting the growth of a micro-organism such as a Gram-negative staining bacterium.

In some embodiments, an anti-microbial agent according to the invention may be one or both of colistin A and colistin B. By "colistin A/B" is meant a polymyxin having anti-microbial activity. In general, colistin A has a molecular weight of about 1169 Da and includes fatty acid moiety 6-methyloctanoyl. Colistin B generally has a molecular weight of 1155 Da and includes fatty acid moiety 6-methylhepatanoyl.

An anti-microbial agent according to the invention may include an anti-microbial agent produced by *Paenibacillus polymyxa* JB05-01-1, ATCC® Accession Number PTA-10436, or by a naturally-occurring bacterium that includes the 16S rRNA sequence of SEQ ID NO:1.

In some embodiments, an anti-microbial agent may include one or more compounds.

An anti-microbial agent may be present in a cell, cell membrane, or crude extract, cell culture, or cell culture supernatant thereof. The cell may be a *Paenibacillus polymyxa* JB05-01-1 cell or a naturally-occurring bacterium that includes the 16S rRNA sequence of SEQ ID NO:1.

Methods of Obtaining and Producing Anti-Microbial Agents

Anti-microbial agent(s) may be obtained from *Paenibacillus polymyxa* JB05-01-1 or from other sources. For example, RE3 (Basic Environmental Systems & Technology Inc. Edmonton, AB, Canada) is a direct-fed microbial product used to improve in vitro ruminal fermentation of barley grain/barley silage-based diets and includes a non-sterile liquid formulation containing *L. paracasei* and *L. lactis* cultures and their fermentation products. *Paenibacillus polymyxa* JB05-01-1 was obtained by culturing a sample of RE3™. Other anti-microbial agents may similarly be found by routine screening for isolates that include the 16S rRNA sequence of SEQ ID NO:1 as described herein or known in the art.

Anti-microbial agent(s) may be produced by growing or culturing *Paenibacillus polymyxa* JB05-01-1 or a bacterium that includes the 16S rRNA sequence of SEQ ID NO:1 in an appropriate cell culture medium under conditions suitable for production of anti-microbial agent(s) as described herein or known in the art. In alternative embodiments, *Paenibacillus polymyxa* JB05-01-1 or a bacterium that includes the 16S rRNA sequence of SEQ ID NO:1 may be grown in an appropriate cell culture medium under conditions suitable for secretion of anti-microbial agent(s) into the cell culture supernatant as described herein or known in the art.

The cell culture medium may be a minimal medium or a complete medium. In some embodiments, the cell culture medium may be LB medium (Luria-Bertani medium). The medium may be a liquid medium or may be a solid or semi-solid medium, such as nutrient broth or agar, or tryptic soy broth or agar. In general, the cell culture medium includes a carbon/energy source, $NH_4$—N, and biotin.

The cell culture conditions (e.g., temperature, time, etc.) may be varied as appropriate to optimize growth and/or production of the anti-microbial agent(s).

In some embodiments, the temperature may range from about 5° C. to about 40° C., such as 10° C., 15° C., 20° C., 25° C., 30° C., or 35° C., or any value therebetween. In alternative embodiments, the temperature may be about 30° C.

In some embodiments, the time may range from about 5 hours to about 48 hours or any value therebetween. In alternative embodiments, the time may be greater than 48 hours. In alternative embodiments, the time may be about 20 hours.

The cell culture conditions may be aerobic or anaerobic.

Standard separation processes may be used to obtain a substantially pure preparation of an anti-microbial agent. An agent or compound is "substantially pure" or "isolated" when it is separated from the components that naturally accompany it. Typically, an anti-microbial agent or compound is substantially pure when it is at least 10%, 20%, 30%, 40%, 50%, or 60%, more generally 70%, 75%, 80%, or 85%, or over 90%, 95%, or 99% by weight, of the total material in a sample. Thus, for example, a substantially pure preparation or culture of a cell expressing an anti-microbial agent, such as a *Paenibacillus polymyxa* JB05-01-1 cell or a naturally-occurring bacterium that includes the 16S rRNA sequence of SEQ ID NO:1, is a preparation of cells or "cell culture" in which contaminating cells that are not a *Paenibacillus polymyxa* JB05-01-1 cell, or do not have the desired 16S rRNA sequence of SEQ ID NO:1, or do not express an anti-microbial agent as described herein, constitute less than 1%, 5%, 10%, 20%, 30%, 40%, or 50%, of the total number of cells in the preparation. In some embodiments, a substantially pure *Paenibacillus polymyxa* JB05-01-1 cell or a substantially pure naturally-occurring bacterium that includes the 16S rRNA sequence of SEQ ID NO:1, is a preparation of cells or "cell culture" that contains 100% of such cells.

In some embodiments, an anti-microbial agent that is isolated by known purification techniques, or isolated as described herein, will be generally be substantially free from its naturally associated components. A substantially pure anti-microbial agent can be obtained, for example, by extraction from a natural source such as a *Paenibacillus polymyxa* JB05-01-1 cell or a naturally-occurring bacterium that includes the 16S rRNA sequence of SEQ ID NO:1.

In some instances, an anti-microbial agent according to the invention will form part of a composition, for example, a crude extract containing other substances. For example, an anti-microbial agent may be present in a crude extract of a *Paenibacillus polymyxa* JB05-01-1 cell or a naturally-occurring bacterium that includes the 16S rRNA sequence of SEQ ID NO:1 that may also contain the other naturally occurring components found in such a cell. A crude extract of a *Paenibacillus polymyxa* JB05-01-1 cell or a naturally-occurring bacterium that includes the 16S rRNA sequence of SEQ ID NO:1 may be prepared by routine procedures, for example, disruption of the cells using standard mechanical or non-mechanical techniques such as freeze-thaw techniques, osmotic shock, enzyme (e.g., lysozyme) treatment, ultrasonication, liquid extrusion, etc., which may be followed by removal of the cell debris by for example centrifugation.

In alternative embodiments, an anti-microbial agent may be present in a cell culture supernatant, such as a supernatant obtained from growing a *Paenibacillus polymyxa* JB05-01-1 cell or a naturally-occurring bacterium that includes the 16S rRNA sequence of SEQ ID NO:1 in a suitable cell culture medium under conditions suitable for secretion of the anti-microbial agent into the supernatant. The term "culture supernatant" refers to the liquid broth remaining when cells grown in a medium are separated from the culture medium by for example centrifugation, filtration, sedimentation, or other means well known in the art. As an example, if the anti-microbial agent(s) is to be isolated from cell culture supernatant, a salt such as ammonium sulphate may be used at various concentrations, initially. Residual ammonium sulphate may then be removed by dialysis against water. The suspended precipitate containing one or more than one antimicrobial compound may be chromatographed on a column such as an ion exchanger, and the various compounds in the culture supernatant may be separated by monitoring absorbance at 280 nm. Active fractions can be determined from among the compounds thus separated, and selected on the basis of the efficacy with which aliquots thereof kill or inhibit the growth of microbes such as bacterial cells, i.e. the indicator strain, known to be sensitive to the anti-microbial agent(s). Active fractions may then be pooled. Further purification may be carried out by high performance liquid chromatography (HPLC) based on the charge of the compound. The various peaks obtained by monitoring absorbance at 280 nm may be separated and again tested for activity against the indicator strain. Purity can be measured using any appropriate method such as column chromatography, gel electrophoresis, HPLC, etc.

The anti-microbial agent may be isolated from the cell culture supernatant using solid phase extraction with columns such as Amberlite XAD-16 column and Sep-Pak C18 Column. The active fraction eluted from the column(s) may be further purified based on molecular weight separation using a Fast Protein Liquid Chromatography (FPLC) system.

A person skilled in the art would understand that other conventional concentration, purification or fractionation methods may be used to obtain one or more isolated or substantially purified anti-microbial agent(s) or partially purified fractions exhibiting an anti-microbial activity from whole or lysed cells or from cell culture supernatant. Typical methods include, without limitation, size exclusion or ion exchange chromatography, ammonium sulfate, alcohol, or chloroform extraction, or centrifugation with size filters.

The anti-microbial activity of an anti-microbial agent may be determined by routine methods or as described herein. For example, anti-microbial activity may be detected by agar diffusion tests or micro-dilution assay.

Pharmaceutical, Veterinary, Nutritional, Cosmetic and Other Uses

Anti-microbial agent(s) according to the invention may be used in a variety of applications in which inhibition of growth of a micro-organism, such as a bacterium, is desirable. Such applications include, without limitation, pharmaceutical and veterinary applications (e.g., for the treatment of a microbial infection), nutritional supplements and animal feed, personal care (cosmetic or hygiene) applications, etc. In alternative embodiments, anti-microbial agent(s) according to the invention may be used to inhibit the growth of a microorganism (e.g., a bacterium) involved in the spoilage of food or other products.

Food spoilage micro-organisms include without limitation one or more species of *Clostridium, Pseudomonas, Porteus, Chromobacterium, Chromobacterium, Lactobacillus, Penicillium, Aspergillus, Rhizopus, Micrococcus, Bacillus, Streptococcus, Pediococcus, Leuconostoc, Chromobacterium, Halobacterium, Alcaigenes, Xanthomonas, Botryitis, Aerobacter, Cornebacterium, Arthrobacter, Microbacterium, Serratia*, etc.

The micro-organism may be a pathogenic micro-organism. The bacterium may a pathogenic bacterium, such as food-borne pathogenic bacterium. Food-borne pathogenic bacteria include without limitation one or more species of *Staphylococcus, Escherichia, Listeria, Salmonella, Streptococcus, Vibrio, Campylobacter, Enterobacter, Shigella*, etc.

The bacterium may include a Gram-negative staining bacterium. Gram-negative staining bacteria include without limitation one or more species of *Escherichia* sp., *Pantoea* sp., *Pseudomonas* sp., *Salmonella* sp., *Shigella* sp., *Helicobacter* sp., *Campylobacter* sp. or *Butyrivibrio* sp., and *Fibrobacter* sp. Examples of Gram-negative bacteria species include without limitation *Escherichia coli* (e.g., *Escherichia coli* RR1, *Escherichia coli* TB1, *Escherichia coli* O157:H7), *Pantoea agglomerans*, *Pseudomonas fluorescens*, *Pseudomonas aeruginosa*, *Salmonella enteritidis*, *Salmonella typhi*, *Shigella dysenteriae*, *Helicobacter pylori*, *Campylobacter jejuni*, *Butyrivibrio fibrisolvens*, or *Fibrobacter succinogenes*.

Other examples of bacteria include without limitation Gram-negative rods such as enteric Gram-negative staining rods, curved Gram-negative staining rods, parvobacteria and *Haemophilus*, Gram-negative staining cocci such as *Neisseria*, non-sporing anaerobes, and bacteria such as spirochaetes, *rickettsia* and *chlamydia*.

Examples of microial infections, such as bacterial infections, include without limitation *chlamydia*, gonorrhea, salmonellosis, shigellosis, tuberculosis, syphilis, bacterial pneumonia, bacterial sepsis (bacteremia), bacterial urinary tract infections, vaginosis, bacterial upper respiratory tract infections, bacterial meningitis, bacterial enteritis, diphtheria, legionellosis, pertussis, scarlet fever, toxic shock syndrome, psittacosis, otitis media, lyme disease, etc.

Pharmaceutical, Veterinary, Nutritional and Other Compositions, Dosages, and Administration Anti-microbial agents of the invention can be provided alone or in combination with other compounds, in the presence of any pharmaceutically, veterinary or cosmetically acceptable carrier, diluent, and/or excipient in a form suitable for administration to animals, for example, humans, cattle, sheep, pigs, poultry, etc. If desired, administration or application of an anti-microbial agent according to the invention may be combined with more traditional and existing anti-microbial therapies, treatments, supplements, or additives, or with other desirable therapies, treatments, supplements, or additives.

Anti-microbial agents according to the invention may be provided chronically or intermittently. "Chronic" administration refers to administration of the anti-microbial agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Conventional pharmaceutical or veterinary practice may be employed to provide suitable formulations or compositions to administer the anti-microbial agent(s) to subjects suffering from or presymptomatic for a microbial infection. Any appropriate route of administration may be employed, for example, parenteral, intravenous, subcutaneous, intramuscular, intracranial, intraorbital, ophthalmic, intraventricular, intracapsular, intraspinal, intrathecal, intracisternal, intraperitoneal, intranasal, intra-anal, intravaginal, aerosol, topical, or oral administration. Therapeutic formulations may be in the form of liquid solutions, syrups, or suspensions; for oral administration, formulations may be in the form of tablets or capsules; and for intranasal formulations, in the form of powders, nasal drops, or aerosols; and topical formulations may come in the form of balms, creams, and lotions.

Methods well known in the art for making formulations are found in, for example, "Remington's Pharmaceutical Sciences" ($19^{th}$ edition), ed. A. Gennaro, 1995, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. For therapeutic or prophylactic compositions, the anti-microbial agent(s) are administered to a subject in an amount sufficient to inhibit the growth of a micro-organism.

An "effective amount" of an anti-microbial agent(s) according to the invention includes a therapeutically effective amount or a prophylactically effective amount. A "therapeutically effective amount" refers to an amount effective, at dosages and for periods of time necessary, to achieve the desired therapeutic result, such as inhibition of the growth of a micro-organism. A therapeutically effective amount of an anti-microbial agent(s) may vary according to factors such as the disease state, age, sex, and weight of the individual or subject, and the ability of the anti-microbial agent(s) to elicit a desired response in the individual or subject. Dosage regimens may be adjusted to provide the optimum therapeutic or prophylactic response. A therapeutically effective amount is also one in which any toxic or detrimental effects of the anti-microbial agent(s) are outweighed by the therapeutically beneficial effects. A "prophylactically effective amount" refers to an amount effective, at dosages and for periods of time necessary, to achieve the desired prophylactic result, such as such as inhibition of the growth of a micro-organism. Typically, a prophylactic dose is used in subjects prior to or at an earlier stage of disease, so that a prophylactically effective amount may be less than a therapeutically effective amount. An exemplary range for therapeutically or prophylactically effective amounts of an anti-microbial agent(s) may be any value from about 0.1 nM to about 0.1M, for example about 0.1 nM to about 0.05M, about 0.05 nM to about 15 µM or about 0.01 nM to about.

It is to be noted that dosage values may vary with the severity of the condition to be alleviated. For any particular subject, specific dosage regimens may be adjusted over time according to the individual need and the professional judgment of the person administering or supervising the administration of the anti-microbial agent(s). Dosage ranges set forth herein are exemplary only and do not limit the dosage ranges that may be selected by medical or veterinary practitioners. The amount of active anti-microbial agent(s) in the composition may vary according to factors such as the disease state, age, sex, and weight of the individual. Dosage regimens may be adjusted to provide the optimum therapeutic or prophylactic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. As used herein, a subject may be a mammal, an agricultural (e.g., farm) or domestic animal, an experimental animal or any animal that may benefit from the anti-microbial agents as described herein. For example, a subject may include a human, non-human primate, rat, mouse, cow, horse, pig, sheep, goat, chicken, turkey, duck, goose, dog, cat, fish, crustacean, etc.

In general, anti-microbial agent(s) of the invention should be used without causing substantial toxicity. Toxicity of the anti-microbial agent(s) of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the anti-microbial agent(s).

In alternative embodiments, an "effective amount" of an anti-microbial agent according to the invention includes an amount effective to inhibit the growth of a micro-organism, such as a bacterium. It is to be understood that such amounts need not be therapeutic or prophylactic amounts, as long as the amount of the anti-microbial agent is capable of inhibiting the growth of a micro-organism, such as a bacterium, in the context in which it is administered or applied, for example, for prevention of food spoilage, etc.

In alternative embodiments, an anti-microbial agent according to the invention may be provided in a cell, for example a substantially pure *Paenibacillus polymyxa* JB05-01-1 cell or a substantially pure naturally-occurring bacterium that includes the 16S rRNA sequence of SEQ ID NO:1, or a cell culture thereof. The cell may be provided in a liquid, or may be frozen or dried, e.g., freeze-dried. The cell culture may be concentrated. The cell culture may be a "starter" culture for example for a dairy product (e.g., milk, cheese, etc.), or for selective media in a laboratory.

The anti-microbial agent may be provided in a therapeutic, veterinary, hygiene, cosmetic, food, drink or feed product. In alternative embodiments, the anti-microbial agent may be provided in the packaging material for, for example, a therapeutic, veterinary, hygiene, cosmetic, food, drink or feed product. The packaging material may include without limitation, plastic, film, Styrofoam, etc.

In alternative embodiments, an anti-microbial agent according to the invention may be provided in a kit that may optionally include additional anti-microbial agents or desirable therapies, treatments, supplements, or additives, optionally with instructions for use thereof.

In alternative embodiments, an anti-microbial agent according to the invention may be provided as a nutritional or food additive, or feed supplement or additive.

A "nutritional additive" or "food additive" refers to a substance that is added to food, generally to affect the characteristics of the food, such as spoilage. A food additive may be "direct" in that it is directly added to food for example to inhibit growth of a micro-organism. A food additive may be considered "indirect" when it is exposed to food during processing, packaging, or storage but is not present in the final food product. The term "feed additive" or "feed supplement" refers to products used in animal nutrition for purposes of improving the quality of feed, or to improve the animals' performance and health, e.g. providing enhanced digestibility of the feed materials or inhibiting the growth of micro-organisms. An example of an animal feed additive is a direct-fed microbial product which refers to a mono or mixed culture of live micro-organisms, which when applied to a host affects beneficially the host by improving the properties of the indigenous microflora. A non-limiting example of a direct-fed microbial product is RE3™ from Basic Environmental Systems & Technology Inc. Edmonton, AB, Canada. In some embodiments, RE3™ may be specifically excluded from a feed additive according to the invention.

A probiotic candidate should display the ability to survive under gastrointestinal tract conditions, namely resistance to salivary lysozyme, gastric acid (HCl) and bile. The "candidate" should also be able to establish itself among the intestinal microbiota and adherence to the intestinal epithelium is considered a major parameter determining candidate's ability to colonize the intestinal tract and thus be effective as a probiotic. As shown in the Examples, *P. polymyxa* JB05-01-1 exhibited probiotic characteristics such as production of antimicrobials (FIGS. 7A and 7B), resistance to gastrointestinal conditions (e.g. lysozyme and acidic pH—Table 5) and tolerance of hydrogen peroxide (Table 5), as well as adhesion to Caco-2 cells (Table 7). Therefore in alternative embodiments, the bacterium, cell culture, supernatant, or the anti-microbial agent according to the invention may be used as a probiotic.

In alternative embodiments, anti-microbial agents of the invention can be provided in combination with other feed or nutritional supplements or additives. For example, at least one supplement or additive, such as listed herein, can be included for consumption with the anti-microbial agent of the invention and may have, for example, antioxidant, dispersant, antimicrobial, or solubilizing properties.

A suitable antioxidant is, for example, vitamin C, vitamin E or rosemary extract. A suitable dispersant is, for example, lecithin, an alkyl polyglycoside, polysorbate 80 or sodium lauryl sulfate. A suitable antimicrobial is, for example, sodium sulfite or sodium benzoate. A suitable solubilizing agent is, for example, a vegetable oil such as sunflower oil, coconut oil, and the like, or mono-, di- or tri-glycerides. Additives include vitamins such as vitamin A (retinol, retinyl palmitate or retinol acetate), vitamin B1 (thiamin, thiamin hydrochloride or thiamin mononitrate), vitamin B2 (riboflavin), vitamin B3 (niacin, nicotinic acid or niacinamide), vitamin B5 (pantothenic acid, calcium pantothenate, d-panthenol or d-calcium pantothenate), vitamin B6 (pyridoxine, pyridoxal, pyridoxamine or pyridoxine hydrochloride), vitamin B12 (cobalamin or cyanocobalamin), folic acid, folate, folacin, vitamin H (biotin), vitamin C (ascorbic acid, sodium ascorbate, calcium ascorbate or ascorbyl palmitate), vitamin D (cholecalciferol, calciferol or ergocalciferol), vitamin E (d-alpha-tocopherol, d-beta-tocopherol, d-gamma-tocopherol, d-delta-tocopherol or d-alpha-tocopheryl acetate) and vitamin K (phylloquinone or phytonadione). Other additives include minerals such as boron (sodium tetraborate decahydrate), calcium (calcium carbonate, calcium caseinate, calcium citrate, calcium gluconate, calcium lactate, calcium phosphate, dibasic calcium phosphate or tribasic calcium phosphate), chromium (GTF chromium from yeast, chromium acetate, chromium chloride, chromium trichloride and chromium picolinate) copper (copper gluconate or copper sulfate), fluorine (fluoride and calcium fluoride), iodine (potassium iodide), iron (ferrous fumarate, ferrous gluconate or ferrous sulfate), magnesium (magnesium carbonate, magnesium gluconate, magnesium hydroxide or magnesium oxide), manganese (manganese gluconate and manganese sulfate), molybdenum (sodium molybdate), phosphorus (dibasic calcium phosphate, sodium phosphate), potassium (potassium aspartate, potassium citrate, potassium chloride or potassium gluconate), selenium (sodium selenite or selenium from yeast), silicon (sodium metasilicate), sodium (sodium chloride), strontium, vanadium (vanadium sulfate) and zinc (zinc acetate, zinc citrate, zinc gluconate or zinc sulfate). Other additives include amino acids, peptides, and related molecules such as alanine, arginine, asparagine, aspartic acid, carnitine, citrulline, cysteine, cystine, dimethylglycine, gamma-aminobutyric acid, glutamic acid, glutamine, glutathione, glycine, histidine, isoleucine, leucine, lysine, methionine, ornithine, phenylalanine, proline, serine, taurine, threonine, tryptophan, tyrosine and valine. Other additives include animal extracts such as cod liver oil, marine lipids, shark cartilage, oyster shell, bee pollen and d-glucosamine sulfate. Other additives include unsaturated free fatty acids such as γ-linoleic, arachidonic and α-linolenic acid, which may be in an ester (e.g. ethyl ester or triglyceride) form. Other additives include herbs and plant extracts such as kelp, pectin, *Spirulina*, fiber, lecithin, wheat germ oil, safflower seed oil, flax seed, evening primrose, borage oil, blackcurrant, pumpkin seed oil, grape extract, grape seed extract, bark extract, pine bark extract, French maritime pine bark extract, muira puama extract, fennel seed extract, dong quai extract, chaste tree berry extract, alfalfa, saw *palmetto* berry extract, green tea extracts, *angelica*, catnip, cayenne, comfrey, garlic, ginger, *ginseng*, goldenseal, juniper berries, licorice, olive oil, parsley, peppermint, rosemary extract, valerian, white willow, yellow dock and yerba mate. Other additives include miscellaneous substances such as menaquinone, choline (choline bitartrate), inositol, carotenoids (beta-carotene, alpha-carotene, zeaxanthin, cryptoxanthin or lutein), para-aminobenzoic acid, betaine HCl, free omega-3 fatty acids and their esters, thiotic acid (alpha-lipoic acid), 1,2-dithiolane-3-pentanoic acid, 1,2-dithiolane-3-valeric acid, alkyl polyglycosides, polysorbate 80, sodium lauryl sulfate, flavanoids, flavanones, flavones, flavonols, isoflavones, proanthocyanidins, oligomeric proanthocyanidins, vitamin A aldehyde, a mixture of the components of vitamin $A_2$, the D Vitamins ($D_1$, $D_2$, $D_3$ and $D_4$) which can be treated as a mixture, ascorbyl palmitate and vitamin $K_2$.

The supplement or additive may be packaged for consumption in softgel, capsule, tablet or liquid form. It can be supplied in edible polysaccharide gums, for example carrageenan, locust bean gum, guar, tragacanth, cellulose and carboxymethylcellulose. Cosmetic or hygiene supplements may be provided in for example, shampoos, conditioners, creams, pastes, lotions, lipsticks, lip balms, etc.

The present invention will be further illustrated in the following examples.

EXAMPLES

The following examples are intended to illustrate embodiments of the invention and should not be construed as limiting.

Example 1: Identification of Antimicrobial Agent Producing Strains

Bacterial Strains and Growth Media

The bacterial indicator strains used are listed in Table 1. All were maintained at −80° C. in appropriate media containing 10% glycerol (w/v). *P. polymyxa* and all indicator strains except *Butyrivibrio fibrisolvens* and *Fibrobacter succinogenes* were propagated aerobically at 30° C. in their respective culture media as indicated in Table 1. The media used were: Tryptic soy broth (TSB) (Difco Laboratories, Sparks, Md., USA), de Man, Rogosa and Sharpe broth (MRS) (Rosell Institute, Montreal, PQ, Canada) (de Man et al. 1960) and Luria-Bertani (LB) broth. Liquid or solid (1.2% w/v agar) anaerobic L-10 medium containing glucose, maltose and soluble starch as carbon sources (each at 0.1% w/w) was used for the growth of *B. fibrisolvens* and *F. succinogenes* (Caldwell and Bryant 1966). Their growth was carried out at 39° C. in a $CO_2:H_2$ atmosphere (95:5 v/v). Before starting the experiments, all strains were sub-cultured at least three times at 24-h intervals using 1% volume transfers.

Isolation and Identification of Antimicrobial-Compound-Producing Bacteria

The antimicrobial agent producer *P. polymyxa* JB05-01-1 was isolated from a direct-fed microbial product (RE3™ Basic Environmental Systems & Technology Inc. Edmonton, AB, Canada). RE3™ was screened for bacteria producing compounds inhibiting the growth of *E. coli* by a deferred antagonism plating procedure as described by Tagg et al. (1976). Briefly, 100 µl of $10^3$-$10^4$ dilutions of RE3™ in L-10 or TSB media were spread on L-10 or TSB plates and incubated overnight at 39° C. and 37° C. The plates were replicated, and then the bacterial colonies on the original plates were washed from the agar surface and the plates were surface sterilized under Ultraviolet (UV) light at 254 nm for 20 minutes. The plates were then overlaid with 5 ml of melted LB (0.5% agar) containing 50 µl of an overnight culture of *E. coli* RR1 and incubated overnight at 37° C. Colonies producing clearing zones were identified and picked from the replica plates for testing for activity against *E. coli* O157:H7.

Gram staining, motility, catalase and oxidase tests were conducted as a preliminary step in the characterization of the selected colonies. Tentative identifications were confirmed by amplification and sequencing of 16S ribosomal RNA genes.

DNA Extraction

The *Paenibacillus* strain (JB05-01-1) was grown in 3 ml of TSB at 30° C. overnight. The cells were harvested by centrifugation at 5000×g for 5 min. DNA was extracted using a Power Soil DNA Kit (MoBio Laboratories Inc., Carlsbad, Calif., USA) according to the manufacturer's instructions. The DNA concentration was measured using the PicoGreen dsDNA quantitation kit (Molecular Probes, Invitrogen, Eugene, Oreg., USA) in a Multi Detection Microplate Reader (Model SIAFRM, BioTek Instruments, Winooski, Vt., USA) using calf *thymus* DNA (Sigma-Aldrich, St. Louis, Mo., USA) as the standard.

Polymerase Chain Reaction Amplification of 16S rRNA Genes

The PCR amplification targeted the approximately 1500 bp of the 16S rRNA gene. The PCR reaction contained 10 ng of template DNA, 2.5 ml of 10× dilution buffer, 10 pmol of each primer and 1 U of Taq polymerase (Takara Shuzo, Japan) in a final volume of 25 ml. The primers used were the universal bacterial primers 8-27 F (5'-AGA GTT TGA TCC TGG CTC)AGA-3° (Liu et al., 1997) and 1492R (5'-TAC CTT GTT ACG ACT T-3') (Kane et al., 1993). The amplification conditions involved denaturation at 95° C. for 1 min, followed by 25 cycles of 95° C. for 30 s, 55° C. for 30 s and 72° C. for 1.5 min. The nomenclature of the primers used was based on *E. coli* numbering system.

Cloning and Sequencing of 16S rRNA Genes

Amplicons from the PCR reaction were electrophoresed on 1% agarose gel and purified by excising the correct sized bands. The DNA was extracted from the gel using QIAquick PCR purification Kit (QIAGEN, Valencia, Calif.) according to the manufacturer's instructions. The purified DNA was cloned into TOPO vector (Invitrogen, Carlsbad, Calif.) and further used to transform electrocompetent *E. coli* (DH5-α cells) by electroporation. The cells were then plated on LB/Kanamycin (50 mg/L) agar plates and incubated overnight at 37° C. Three clones, verified for correct inserts, were grown overnight in LB/Kanamycin (100 mg/L). All clones were sequenced by the University of Calgary Core DNA Services, Calgary, AB, Canada. The 16S rRNA sequence was a consensus from three clones. The 16S rDNA sequences of the isolates were compared with DNA sequences from the National Center for Biotechnology Information (NCBI) database using the standard nucleotide-nucleotide homology search Basic Local Alignment Search Tool (BLAST) (Altschul et al., 1990).

Results

Sequencing of the 16S rDNA PCR products from the isolate showing the highest activity against *E. coli* O157:H7 identified an organism that shared 99% homology with *Paenibacillus polymyxa*. This isolate was designated as *Paenibacillus polymyxa* JB05-01-1. The 16S rRNA gene partial sequence of *P. polymyxa* JB05-01-1 was deposited with GenBank and has been assigned Accession Number GQ184435 (FIG. 4, SEQ ID NO: 1).

TABLE 1

Antimicrobial spectrum of inhibitory substance produced by *Paenibacillus polymyxa* JB05-01-1 culture supernatant (CS-JB05-01-1) and polymyxin B, used as positive control.

| | | | Inhibition* | |
|---|---|---|---|---|
| Indicator strains | Source | Medium | CS-JB05-01-1 | Polymyxin B (0.1 µg ml$^{-1}$) |
| *Bacillus circulans* | LRC 9E2 | LB | − | − |
| *Bacillus lecheniformis* | LRC 8422 | LB | − | − |
| *Butyrivibrio fibrisolvens* | LRC OR85 | L-10 | + | + |
| *Escherichia coli* | LRC RR1 | TSB | +++ | +++ |
| *Escherichia coli* | LRC TB1 | TSB | ++ | +++ |
| *Escherichia coli* | LRC SA1650 | TSB | ++ | ++ |
| *Enterococcus mundtii* | LRC 8369 | LB | − | − |
| *Fibrobacter succinogenes* | ATCC 19169 | L-10 | + | + |
| *Lactococcus lactis* | ATCC 7962 | MRS | − | − |
| *Listeria innocua* | HPB 13 | TSB | − | − |
| *Listeria ivanovii* | HPB 28 | TSB | − | − |
| *Pantoea agglomerans* | LRC BC1 | TSB | + | + |
| *Pseudomonas fluorescens* | LRC R73 | TSB | ++ | ++ |
| *Paenibacillus polymyxa* | ATCC 43865 | LB | − | − |
| *Paenibacillus polymyxa* | ATCC 7070 | LB | − | − |
| *Paenibacillus polymyxa* JB05-01-1 | This study | LB | − | − |
| *Pediococcus acidilactici* | ATCC 25740 | MRS | − | − |

TABLE 1-continued

Antimicrobial spectrum of inhibitory substance produced by *Paenibacillus polymyxa* JB05-01-1 culture supernatant (CS-JB05-01-1) and polymyxin B, used as positive control.

| | | | Inhibition* | |
|---|---|---|---|---|
| Indicator strains | Source | Medium | CS-JB05-01-1 | Polymyxin B (0.1 µg ml$^{-1}$) |
| *Pediococcus pentosaceus* | ATCC 25745 | LB | – | – |
| *Streptococcus bovis* | ATCC 33317 | LB | – | – |

*Determined from two individual assays
– No inhibition at concentrations up of 0.1 µgml–1.
+ Diameter of the inhibition zone 10 ± 2 mm
++ Diameter of the inhibition zone 16 ± 2 mm
+++ Diameter of the inhibition zone 28 ± 2 mm
ATCC: American Type Culture Collection,
LRC: Lethbridge Research Center
HPB: Health Product Branch, (Health and Welfare Canada, Ottawa, ON, Canada)

Example 2: Production of the Antimicrobial Agent

One liter of LB medium was inoculated with 10 ml of a fresh, overnight culture of *P. polymyxa* JB05-01-1 and incubated at 30° C. with agitation at 200 rpm. The culture optical density at 600 nm was measured every two hours using a Multi-detection micro-plate reader (Bio-Teck instrument Inc., Winooski, Vt., USA), and 1 mL of culture was centrifuged (8,000 rpm, 10 min, 4° C.) to remove the cells. The supernatant was heated at 70° C. for 10 min to inactivate any protease activity, as described by Martin et al. (2003). The agar diffusion assay and micro-dilution method were used to test the heated supernatants for antimicrobial activity as described herein.

The determination of soluble protein was done using the Folin phenol reagent method as described by Lowry et al. (1951) with bovine serum albumin as standard. Polymyxin E, Polymyxin B and Nisin A were used as positive control for antimicrobial activity. Nisin A stock solutions were prepared from pure Nisin obtained from Aplin and Barrett (Beaminster, UK) in the form of Nisaplin™, which contains 2.5% (w/w) Nisin A. Polymyxin E and Polymyxin B were purchased from Sigma-Aldrich (Oakville, ON, Canada).

Inhibition of *Escherichia coli* RR1 by supernatant of a batch culture grown in Luria-Bertani broth, measured by the micro-dilution method, was maximal at 20 h and remained so through 48 h. Thus, based on agar diffusion and micro-dilution tests, the secretion of the antimicrobial agent was shown to start in the exponential phase and reach its maximum in the early stationary phase (FIG. 1). Production thus appeared to be growth associated and activity levels remained stable through 48 h Inhibition zone diameters at 48 h were approximately 8±1 mm and activity was 96 AU ml$^{-1}$.

Example 3: Spectrum of Activity

The qualitative antimicrobial spectrum of *P. polymyxa* culture supernatant was determined using the agar well diffusion method (Wolf and Gibbons 1996). Briefly, a 25-ml volume of molten tryptic soy agar (0.75% agar w/v) was cooled to 47° C. and seeded with 1% (v/v) overnight TSB culture of an indicator strain. The seeded agar was then poured into a sterile Petri plate and allowed to solidify at room temperature. Wells (7 mm) were cut in the solidified agar using a sterile metal cork borer and filled with 80 µl of supernatant. The plates were left at 5° C. for 2 h to allow diffusion of the tested aliquot and then incubated aerobically for 18 h at 30° C. Absence or presence of inhibition zones as well as their diameters were recorded.

The antimicrobial activity was also determined by the micro-dilution method described by Daba et al. (1994). Activity was expressed in arbitrary units per milliliter (AU ml$^{-1}$) using the formula (1000/125)×(1/D), where D was the highest dilution causing inhibition of the indicator strains.

The minimum inhibitory concentration (MIC) of *P. polymyxa* JB05-01-1 culture supernatant and pure polymyxin E or polymyxin B against *E. coli* RR1 was determined using a Microtest™ polystyrene micro-plate assay (96-well, Becton Dickinson Labware, Lincoln Park, N.J.) as described by Kheadr et al. (2004).

The inhibitory spectrum of the culture supernatant is presented in Table 1. Gram-negative staining bacteria (*E. coli* RR1, *Pantoea agglomerans* BC1, *Pseudomonas fluorescens* R73, *B. fibrisolvens* OR85 and *F. succinogenes* S85) were inhibited while no activity was detected against Gram-positive staining bacteria. The spectrum of activity of the antimicrobial agent produced by *P. polymyxa* JB05-01-1 was different from that of Nisin A but similar to polymyxin E and polymyxin B used as a positive control (Table 1).

To determine the effect of *P. polymyxa* JB05-01-1 culture supernatant, *E. coli* RR1 cells were cultivated in the presence of concentrated *P. polymyxa* culture supernatant containing JB05-01-1 at final total activity of 0, 32, and 96 AU/ml. The $OD_{600nm}$ of culture was determined every two hours using a multi-detection microplate reader (Bio-Teck instrument Inc, Winooski, Vt., USA). The corresponding final cell concentration expressed as CFU/ml was determined as described by Naghmouchi et al. (2008). The inhibitory activity (I.A.) of culture supernatant containing JB05-01-1 was calculated as a percentage, I.A.=100-100 $[OD_{600}(x)/OD_{600}(i)]$, where (x) is culture supernatant containing JB05-01-1 at the corresponded total activity and (i) is the control culture. Data was reported as means of duplicate analyses.

To determine the mode of action of culture supernatant containing JB05-01-1, the viability of *E. coli* RR1 cells was examined (FIG. 2) upon their contact with culture supernatant containing JB05-01-1. Thus, addition of culture supernatant containing JB05-01-1 at total activity of 32 or 96 AU/ml reduced the final cells concentrations of *E. coli* RR1 by about 2.7 and 3.4 $\log_{10}$ CFU/ml after 2 h of exposure, respectively (graph B). The corresponding inhibitory activities were estimated to 47.1% and 51%, respectively. The $OD_{600nm}$ of the cell suspension was constant through the experiments (graph A). The data obtained indicates that *P. polymyxa* JB05-01-1 has bactericidal action like polymyxin B, which was used as a positive control.

Example 4: Characterization of the Antimicrobial Agent

The sensitivities of the antimicrobial agent to proteases (all from Sigma-Aldrich, Oakville, ON) or other agents was tested by treating *P. polymyxa* JB05-01-1 culture supernatant with 2 mg ml$^{-1}$ final concentration of proteinase K (Tritirachium album), α-chymotrypsin (bovine pancreas), lipase (Sigma-Aldrich, Oakville, ON), trypsin (porcine pancreas), urea (Sigma-Aldrich, St. Louis Mo.), sodium dodecyl sulfate (SDS) (Sigma-Aldrich, St. Louis Mo.) for 1 h at 37° C. (Motta et al. 2007). Thermal stability of the antimicrobial activity was determined by holding aliquots (1000 μl) of 20 h culture supernatant at temperatures ranging from 50° C. to 90° C. for 30 min or at 100° C. for 10 min. The effect of pH was determined by adjusting the pH of *P. polymyxa* JB05-01-1 culture supernatant from 2 to 9 using 5 M HCl or NaOH. The activity of each sample was compared with the activity of untreated *P. polymyxa* JB05-01 culture supernatant at pH 6.8.

The effect of several organic solvents was evaluated by stirring 20 h culture supernatant for 2 h with 10% (v/v) acetonitrile, hexane, propanol, ethanol, toluene, acetone, butanol or methanol (all solvents were obtained from Sigma-Aldrich, St. Louis Mo.). Residual antimicrobial activities were tested using the agar diffusion assay against *E. coli* RR1 as described herein, with controls for effects of residual solvent.

The effect of enzymes, detergents and other compounds on the anti-*E. coli* activity of the *P. polymyxa* JB05-01-1 culture supernatant is shown in Table 2.

TABLE 2

Inhibition of *Escherichia coli* RR1 by *Paenibacillus polymyxa* JB05-01-1 culture supernatant (CS-JB05-01-1) or polymyxin B treated with enzymes, detergents or urea, as determined by the agar diffusion test.

| | % of residual activity* | |
|---|---|---|
| Treatment agent | CS-JB05-01-1 | Polymyxin B (0.1 μg ml$^{-1}$) |
| None | 100 | 100 |
| Proteinase K | 0 | 4.5 |
| Trypsin | 83.3 | 62.5 |
| Chymotrypsin | 75 | 79.5 |
| Lipase | 62.5 | 58.3 |
| SDS | 66 | 70.1 |
| Urea | 58 | 62.5 |

*Antimicrobial activities of culture supernatant without additives are 100%. Results are means of two individual assays with an SD less than 5% about the mean.

Activity was eliminated after proteinase K treatments. Lipase, trypsin, α-chymotrypsin, sodium dodecyl sulphate (SDS) and urea reduced the antimicrobial activity by 38%, 17%, 25%, 34% and 42% respectively when compared to untreated activity.

The antimicrobial activity remained unchanged after heating at 80° C. for 30 min Loss of activity of about 60% was observed after heating at 90° C. for 30 min. Heating to 100° C. for 10 min completely eliminated the antimicrobial activity.

Organic solvents such as chloroform, propanol, methanol, ethanol and toluene did not affect the activity of the antimicrobial peptide. Acetonitrile or hexane treatment at the same concentration (10%, v/v) reduced the antimicrobial activity by about 5% and 20%, respectively. Activity also remained stable after a two-hour incubation at pH ranging from 2 to 9.

Example 5: Molecular Weight Determination

*P. polymyxa* JB05-01-1 culture supernatant was analysed in duplicate using a NuPAGE 12% Bis-Tris gel kit (Invitrogen, Burlington, ON, Canada) as per manufacturer's instructions at 200 V (constant) for 40 min. The 2.5-200 kDa molecular weight marker kit from Invitrogen was used as a molecular weight standard. After electrophoresis, one gel was stained with Coomassie Brilliant Blue R250 (Invitrogen). A duplicate gel was used for the plate overlay assay to estimate the molecular weight of the antimicrobial compounds as described by Bhunia et al. (1987). Briefly, a SDS-PAGE gel prewashed with sterile water was placed in a Petri dish and overlaid with 10 ml tryptic soy agar containing growing cells of *E. coli* RR1 at about $10^5$ CFU ml$^{-1}$. The agar was allowed to solidify, held at 4° C. for 60 min, and then incubated for 18 h at 30° C. The formation of an inhibition zone indicated the position and size of the active antimicrobial peptide in the gel.

Coomassie Brilliant Blue staining of SDS-PAGE gels of *P. polymyxa* JB05-01-1 culture supernatant revealed no distinct protein bands. However, inhibitory activity was detected as a clearly defined zone of inhibition in the region corresponding to a molecular mass of <2.5 kDa (<2500 Da) after gels were overlaid with *E. coli* RR1-seeded agar (FIG. 3). No inhibitory activity was detected when the SDS gels were overlaid with *Listeria innocua*.

Example 6: Isolation and Purification of Antimicrobial Peptides

Strains and Culture Conditions

The bacterial strains used and their culture media are listed in Table 4. All strains were stored previously at −80° C. in media containing 20% glycerol (w/v) and were subcultured twice in the appropriate media prior to being used in experiments. Fresh cultures were prepared by inoculation of 10 ml of the corresponding medium with 100 μl of the frozen stock followed by incubation for 18-24 h at the corresponding temperature.

*P. polymyxa* JB05-01-1 was grown aerobically at 30° C. in Luria-Bertani (LB) broth (Difco Laboratories, Detroit, Mich., USA) for 16 h. Colistin-sensitive strain *Escherichia coli* RR1 (*E. coli* RR1), was obtained from the Lethbridge Research Center culture collection. *E. coli* RR1 was grown aerobically for 18 h at 30° C. in tryptic soy broth (TSB, Difco Laboratories, USA).

Isolation of Antimicrobial Peptides

*P. polymyxa* JB05-01-1 culture was used to inoculate 500 ml of Luria-Bertani (LB) broth (1% inoculum) in a 1-liter flask and incubated at 30° C. for 20 h. Cells in the fermentation broth were separated by centrifugation (12,000 g, 20 min, 4° C.). The resulting cell-free supernatant was heated (100° C. for 10 min) and passed through a 5×50 cm column (Amersham Pharmacia Biotech) packed with 60 g Amberlite XAD-16 resin (Sigma-Aldrich, Oakville, ON, Canada) via a Gilson MiniPlus 2 Pump at a flow rate of 5 ml/min to remove hydrophobic components from the medium as described by Martin et al. (2003). The Amberlite XAD-16 column was washed with 300 ml of 30% ethanol after which the active fraction was eluted with 500 ml of 70% isopropanol (pH 2; achieved through the addition of 1 M HCl) at a flow rate of 5 ml/min. The eluted active fraction was then evaporated to 30% aqueous volume (approximately 150 ml) using a rotary evaporator (Laborota 4001 Efficient; Krackeler Scientific, Inc., Albany, N.Y., U.S.A.) at 30° C. The Amberlite XAD-16 column was washed with 500 ml of HPLC grade water for future use.

The evaporated active fraction was passed through a Waters Sep-Pak Vac 35 cc C18-10 g column (Waters, Milford, Mass., USA) via Gilson MiniPlus 2 Pump at a flow rate of 2.5 ml/min. The column was washed with 30 ml of 20% acetonitrile ($CH_3CN$) 0.5 M HCl and the active fraction eluted with 50 ml of 50% acetonitrile 0.5 M HCl (Selim et al. 2005). The active fraction eluted from the Sep-Pak C18 column was evaporated under similar conditions as hereinbefore described to 20 ml and further concentrated to 5 ml using Centricon YM-3 centrifugal filter unit (Millipore: Bedford, Mass., USA) at 3000 g for 120 min at 4° C. The evaporated active fraction eluted from the Sep-Pak C18 column was designated as Fraction E.

All fractions obtained at each stage of the isolation process were assessed for antibacterial activity using the micro-dilution method as described below.

Gel Filtration Chromatography Technique

Fraction E was applied to Superdex 75 HR 16/60 gel filtration chromatography to obtain the active fraction based on molecular weight separation. The Superdex 75 HR 16/60 column was equilibrated with 100 mM sodium phosphate extraction buffer (pH 7.4) containing 150 mM NaCl. This step was carried out at 4° C. with a flow rate of 0.5 ml/min using a Fast Protein Liquid Chromatography (FPLC) system (GE Healthcare Canada Inc.). One ml of Fraction E was applied onto the column and fractions of 1 ml were collected during the elution process using an isocratic gradient. The mobile phase consisted of 30% $CH_3CN$/70% HPLC grade water, 0.1% trifluoroacetic acid (TFA) single buffer. Elution was monitored at wavelength detection of 218 nm during a total running time of about 600 min. Fractions exhibiting antibacterial activity, at a given retention time, were collected from different FPLC runs, pooled and lyophilized. The resulting powder was dissolved in 0.1 ml HPLC grade water and checked again for activity against $E.\ coli$ RR 1 and the other bacteria listed in Table 4.

Antibacterial Activity Assay

Antibacterial activity of the fractions obtained at each stage of the isolation process was determined by the micro-dilution method (Daba et al. 1994). Total activity was expressed in arbitrary units per milliliter (AU/ml), using the formula (1000/125)×(1/D), where D was the highest dilution causing complete inhibition of $E.\ coli$ RR1, the indicator strain (Naghmouchi et al. 2010).

Protein Concentration Determination

The determination of soluble protein concentration was performed in triplicate with the Folin phenol reagent method (Lowry et al. 1951). Bovine serum albumin (BSA) was used as internal standard. Polymyxin E solution standard was obtained from Sigma-Aldrich (Oakville, ON, Canada).

Determination of Minimum Inhibitory Concentration

Minimum inhibitory concentration (MIC) for FPLC purified peptide peak (retention time of 361.55 min) and that of polymyxin (colistin—standard) were determined by the micro-dilution assay (Naghmouchi et al. 2010).

MALDI TOF/TOF Analysis

Two microliters of the peak sample obtained from final FPLC purification step (retention time 361.55 min) was analysed directly by over-spotting with 1 μL α-Cyano-4-hydroxycinnamic acid (3 mg/mL containing 1.8 mg/mL ammonium citrate dissolved in 50% ACN/0.1% TFA). In addition, 5 μL of each sample was diluted with 50 μL 0.1% TFA/water C18 Ziptip desalted and eluted with matrix. The samples were air dried and then analysed on an Applied Biosystems MDS Sciex 4800 TOF/TOF Mass Analyser over mass range 600-4000 m/z collecting 500 laser shots. Ions of highest intensity were manually selected for MSMS fragmentation for 1000 laser shots and data acquired.

Manual Nanospray Analysis

Four microliters of the peak sample obtained from final FPLC purification step (retention time 361.55 min) was placed into a silica Au/Pd coated nanoES spray tip (Proxeon, Odense. Denmark). Static manual nanospray was performed on an Applied Biosystems/MDS Sciex QStar Pulsar I fitted with a Protana/Proxeon Nanospray source. Spray was established by applying a tip voltage of 1200V and collecting a TOFMS survey scan 300-1200 m/z consisting of 50 accumulated 1 sec scans. Mass spectrometer parameters used were as follows: Declustering potential setting of 55, Focusing Potential setting of 265, Curtain gas setting of 25 and CAD gas setting of 6 with Nitrogen in the collision cell. The most intense double charged ions were selected for MSMS fragmentation. Product ion scans were acquired over the mass range 100-1500 m/z range and collision energy was manually increased to provide the best fragmentation during the 50 accumulated 1 second scans. Mass spectrometer parameters used for MSMS were as follows: Declustering potential setting of 50, Focusing Potential setting of 220, Curtain gas setting of 25 and CAD gas setting of 7 with Nitrogen in the collision cell.

Isolation, purification and characterization of antimicrobial substance(s) produced by $P.\ polymyxa$ JB05-01

The characterization of antimicrobial substance(s) from Luria-Bertani broth cultured with $P.\ polymyxa$ JB05-01-1 is summarized in Table 3.

TABLE 3

Antimicrobial substance(s) recovery at different stages of purification. Total and partial purified substance(s) were quantified by the micro-dilution test using $E.\ coli$ RR1 as indicator strain.

| Step/fraction | Volume (ml) | Total protein (mg) | Total activity[1] (AU) | Specific activity[2] (AU/mg) | Increase in Specific activity (fold) | Recovery (%) |
|---|---|---|---|---|---|---|
| Supernatant | 500 | 1750 | 48000 | 27.42 | 1 | 100 |
| Amberlate XAD-16 | 200 | 196 | 25600 | 130.61 | 4.8 | 53 |
| Sep-Pack $C_{18}$ eluate | 50 | 3.15 | 6400 | 2031.7 | 74.09 | 13.33 |
| FPLC-system | 1 | 0.05 | 256 | 5120 | 189.62 | 1.06 |

[1]Activity (AU/ml) determined by micro-titer plate assay using $E.\ coli$ RR1 as indicator strain and multiplied by the volume in milliliters.
[2]Activity (AU/ml) divided by total protein (mg).

Extraction of the antimicrobial substance(s) was achieved using Amberlite XAD-16-adsorbent, a non-ionic macro-reticular resin that adsorbs and releases ionic species through hydrophobic and polar interactions (Zengguo et al. 2007). By applying XAD-16 resin to clarified cell-free culture supernatant, the antimicrobial substance(s) was/were selectively adsorbed, whilst other water-soluble components remained in the liquid phase. The antimicrobial substance(s) was/were eluted from XAD-16 by 70% acid and isopropyl alcohol, and the resulting fraction was evaporated to 30% aqueous volume which retained most of the antimicrobial activity. The specific activity obtained after Amberlite XAD-16-adsorbent was approximately 130.61 AU/mg of protein.

The antimicrobial substance(s) was/were subsequently applied to Sep-Pack C18 column and the most active fraction purified with 50% acetonitrile and 0.5 M HCl. The recovery from the Sep-Pack C18 step was 13.3% with the specific activity of 2,032 AU/mg of protein.

Figure 5:
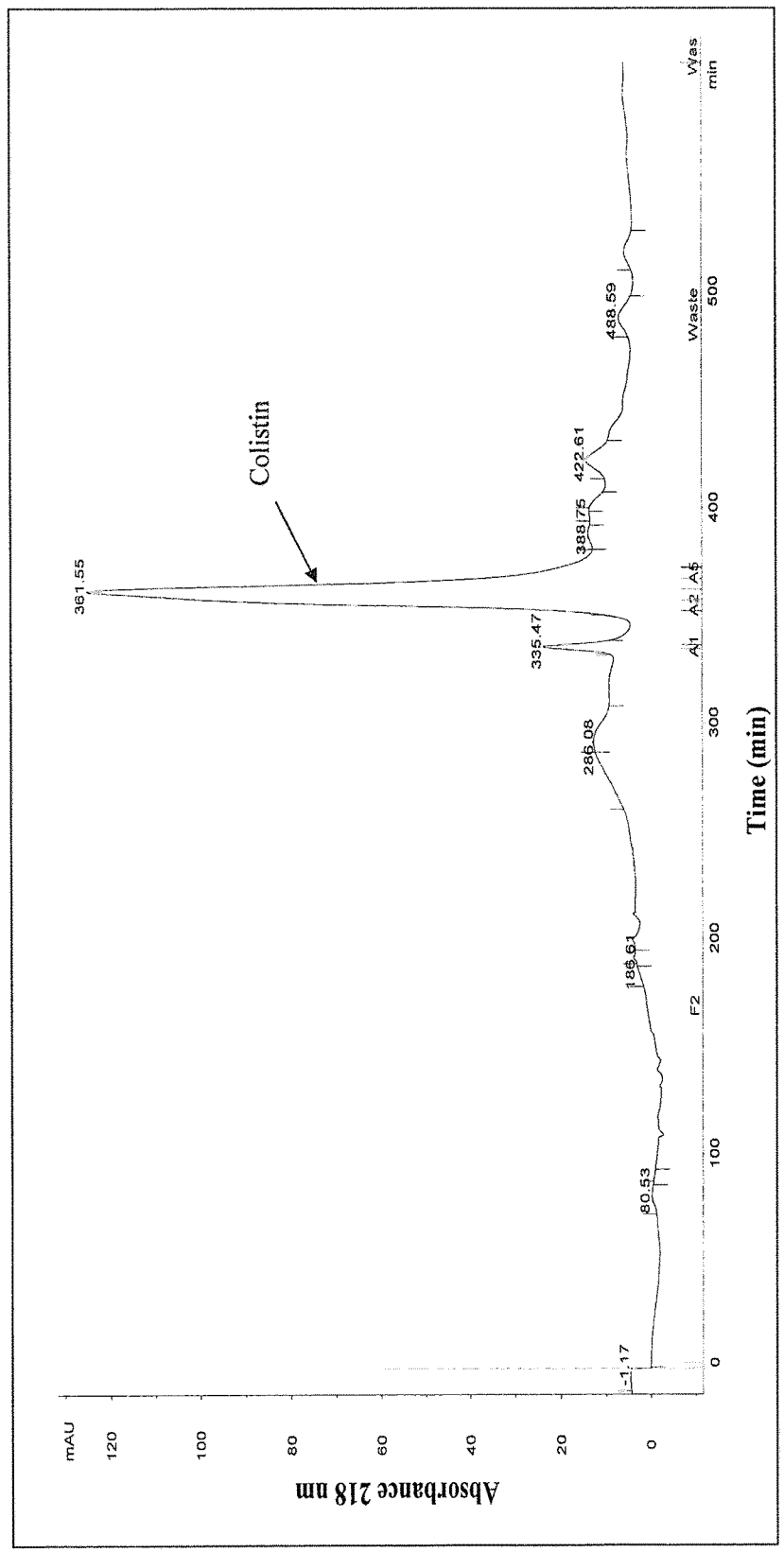
FIG. 5 is a Fast Protein Liquid Chromatography (FPLC) of purified antimicrobials peptides produced by *P. polymyxa* JB05-01-1 eluted at 30% acetonitrile ($CH_3CN$), 1% TFA.

Finally, the antimicrobial fraction obtained from the Sep-Pack C18 recovery step was separated with the FPLC system connected to Hiload 16/60 Superdex 75 Prep grade size exclusion. In the FPLC profile, fractions with a peak retention time (RT) of 361.55 min were identified (FIG. 5). These fractions were active against *E. coli* RR1. Approximately 1.1% of the culture supernatant was recovered as antimicrobial substance(s) through the FPLC filtration process. The procedure increased the specific activity (per mg of protein) of the antimicrobial substance(s) 190-fold. Total purified antimicrobial substance(s) obtained from 500 ml of the fermented broth were approximately 0.05 mg.

The MIC of FPLC purified peptide peak (retention times of 361.55 min) against *E. coli* RR1 was approximately 0.13 µg/ml.

Structure Determination

Figure 6A:
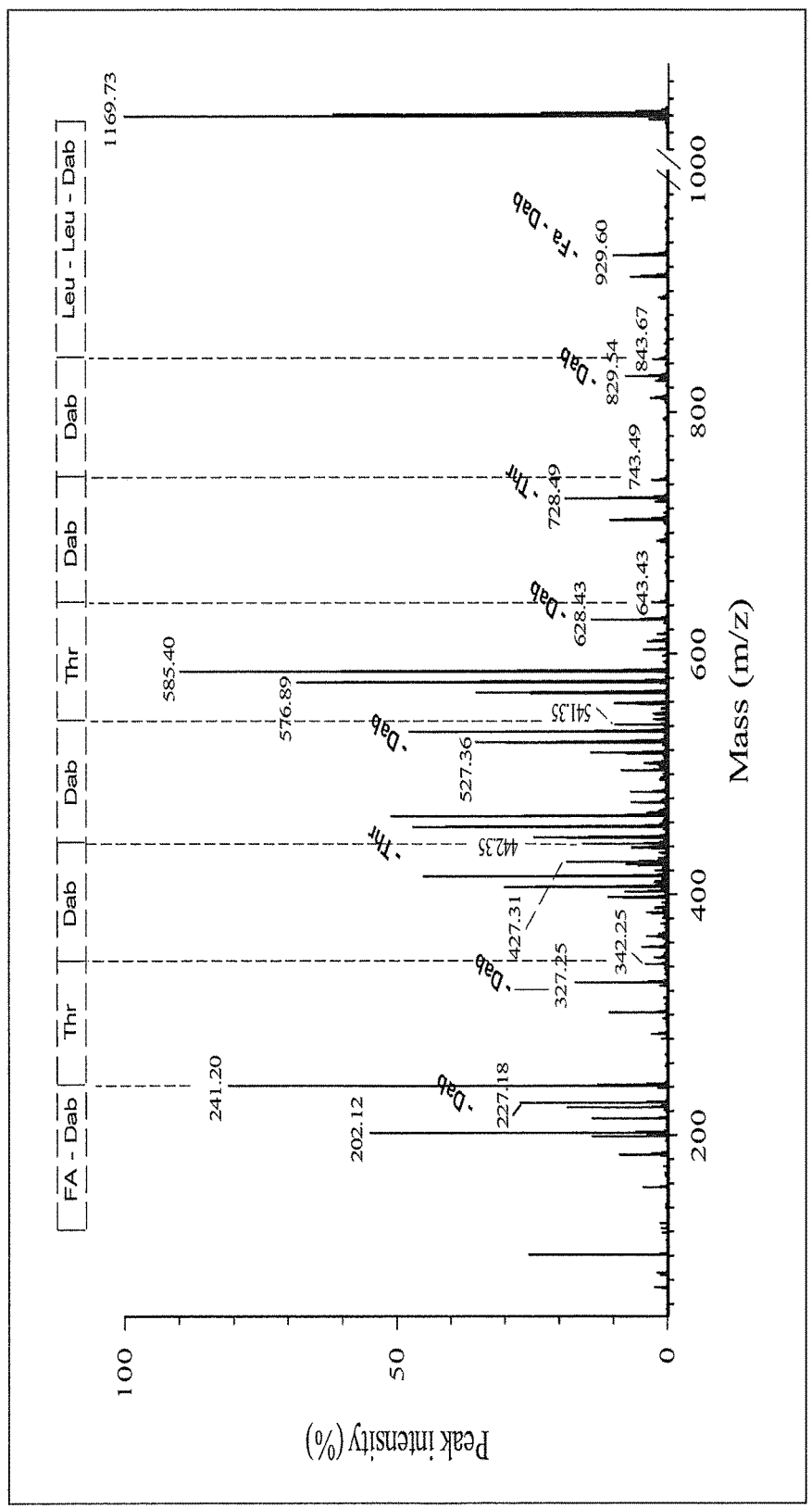
FIG. 6A is a mass spectrometry analysis of purified Colistin A produced by *P. polymyxa* JB05-01-1, and structure determination.

The chemical nature of the antibacterial substance(s) produced by *P. polymyxa* JB05-01-1 was elucidated by MALDI TOF/TOF analysis and Nanospray analysis (FIGS. 6A and 6B) as described below.

Figure 6B:
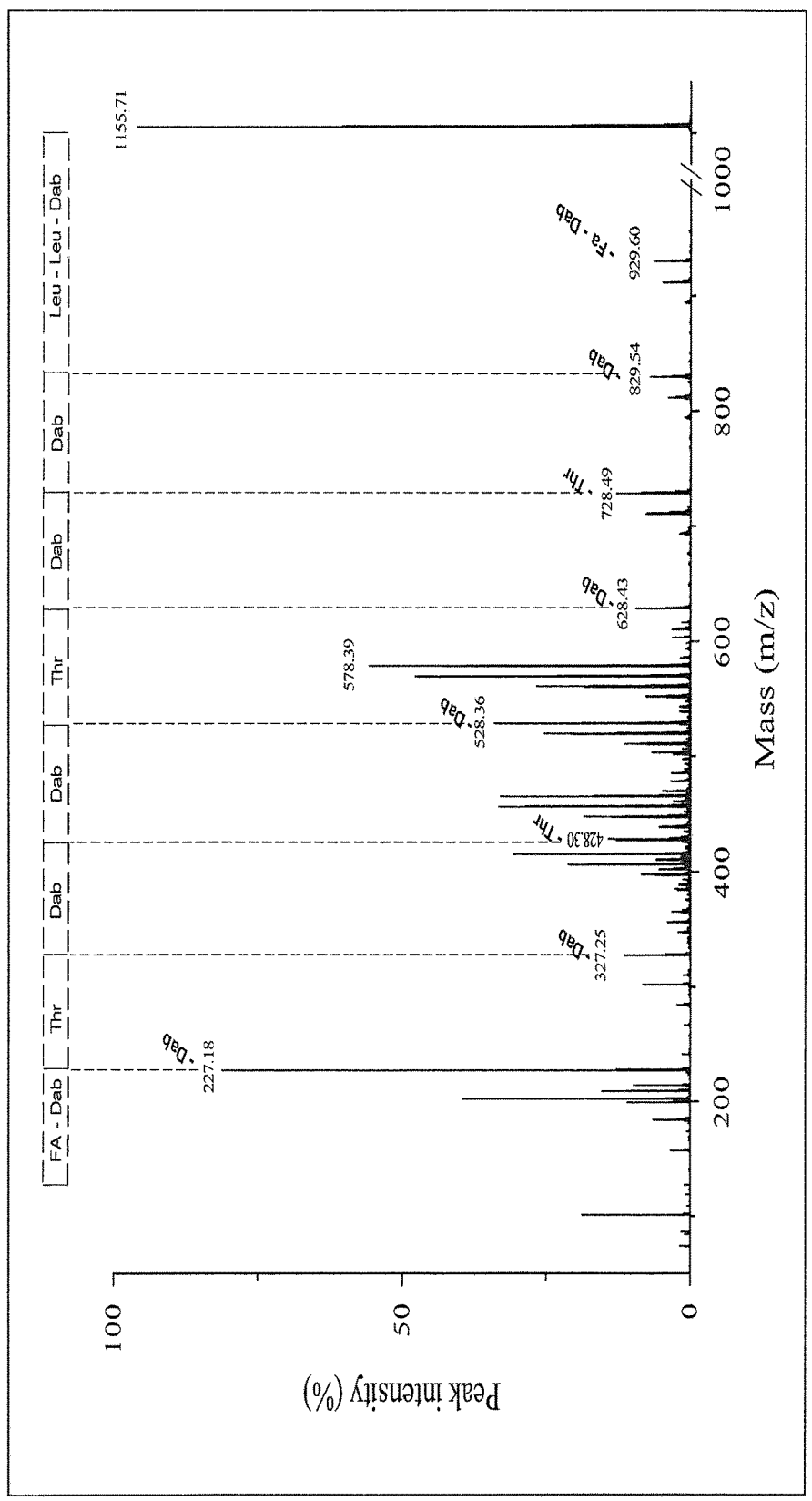
FIG. 6B is a mass spectrometry analysis of purified Colistin B produced by *P. polymyxa* JB05-01-1, and structure determination. Molecular weights were determined using MS analysis (Colistin A: 1169 Da; Colistin B: 1155 Da). MS/MS spectrums relevant to the species at m/z 585.3 and 578.4 observed in the chromatograms of FIG. 6A and FIG. 6B, respectively. The assignments of the different peaks are shown for the corresponding peptide sequence.

Tandem mass spectrometry MS analysis was performed for a single active peak obtained from the final FPLC purification (361.55 min) step. Data analysis revealed the presence of two compounds with the following molecular weights 1169.7 Da (FIG. 6A) and 1155.7 Da (FIG. 6B), which are equivalent to those of colistin A and colistin B. Further confirmation of this structure (colistin) was performed with MS/MS analysis on TOF and ESI. Fragmentation of peak 585.3 Da (A) in the ion trap permitted the identification in the spectrum (FIG. 6A) of the first series of product ions with m/z 829.5, 728.5, 628.4, 527.3, 427.3, 327.2, 227.2, which are formed by subsequent loss of amino acid moieties. Similar results were observed for peak 578.4 Da (FIG. 6B). The m/z ions obtained in the second series were identical to fragmentation patterns reported in the literature (Govaerts et al. 2002; De Crescenzo et al. 2007).

Figure 6C:
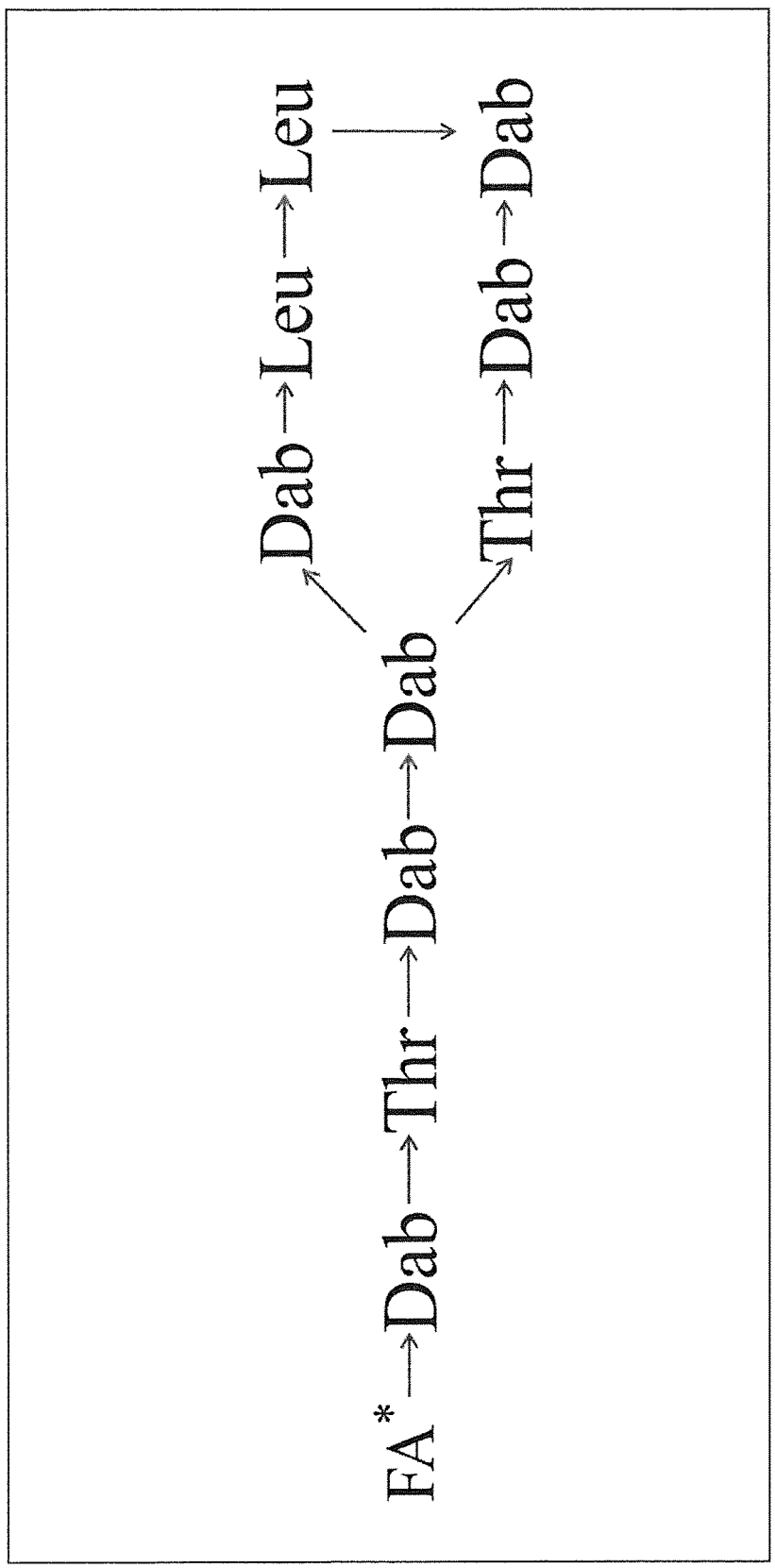
FIG. 6C is a chemical structure of fatty acid (FA): Colistin A, 6-methyloctanoyl; Colistin B, 6-methylhepatanoyl.

FIG. 6C shows the chemical structure of fatty acid colistin A and colistin B. Thus it was concluded that the active antimicrobial substance purified from *P. polymyxa* JB0501 are colistin A and colistin B.

Spectrum of Activity

As shown in Table 4, purified colistin (A/B) produced by *P. polymyxa* JB05-01-1 had inhibitory activity against Gram-negative bacteria including *E. coli* O157:H7, *E. coli* RR1, *Pseudomonas fluorescens* R73 and *Pseudomonas aeruginosa*. The MIC values of the purified peptides were about 0.13 and 0.162 µg/ml for *E. coli* O157:H7 and *P. fluorescens* LRC R73, respectively. Similar MIC values were obtained with the colistin standard.

TABLE 4

Antimicrobial spectrum and minimal inhibitory concentration (MIC) of purified peptide (colistins A and B) produced by *Paenibacillus polymyxa* JB05-01-1

| Indicator strains | Source | Growth Medium | Inhibition zone* attributed to Purified peptide at (5 µg/ml) | MIC (µg/ml) |
|---|---|---|---|---|
| *Listeria ivanovii* | HPB28 | TSB | – | 2.5-5 |
| *L. monocytogenes* | LSD530 | TSB | – | 5-10 |
| *Escherichia coli* | MC4100 | TSB | ++ | 0.13-0.26 |
| *E. coli* O157:H7 | ATCC 35150 | TSB | ++ | 0.13 |
| *E. coli* | ATCC 25922 | TSB | ++ | 0.13 |
| *E. coli* | RR1 | TSB | +++ | 0.13 |
| *Pseudomonas aeruginosa* | ATCC 19442 | TSB | +++ | 0.52 |
| *P. fluorescens* | LRC R73 | TSB | +++ | 0.162 |
| *Lactococcus lactis* | UL719 | MRS | – | – |
| *Paenibacillus polymyxa* | ATCC 43865 | MRS | – | – |
| *Pediococcus acidilactici* | UL5 | MRS | – | – |
| *Salmonella enterica* | UL | TSB | + | 1.04-2.08 |
| *Staphylococcus aureus* | Scott A3 | TSB | – | – |

*Determined from two individual assays
–: No inhibition at concentrations up of 5 µg ml$^{-1}$
+: Diameter of the inhibition zone 10 ± 2 mm
++: Diameter of the inhibition zone 16 ± 2 mm
+++: Diameter of the inhibition zone 28 ± 2 mm
ATCC: American Type Culture Collection;
UL: University Laval, Quebec, Canada
LRC: Lethbridge Research Center, Alberta, Canada;
LSD: Laboratory Services Division, Ottawa, ON, Canada; HPB: Health Product Branch, (Health and Welfare Canada, Ottawa, ON, Canada).
MRS: de Man-Rogosa and Sharpe medium
TSB: Tryptone Soya Broth medium Example 7: Determination of the Potential of *P. polymyxa* JB05-01-1 as a Probiotic Strains and Culture Conditions

*Paenibacillus polymyxa* JB05-01-1 and *Paenibacillus polymyxa* reference strains ATCC (43865 and 7070) were aerobically grown for 18 h at 30° C. with agitation in Tryptic Soy Broth (TSB) (Difco Laboratories, Detroit, Mich., USA) containing 1% of yeast extract leading to a medium named TSBYE. *Escherichia coli* generic ATCC 25922 (*E. coli* ATCC 25922) was grown for 16 h at 37° C. in TSB (Difco). The four strains were stored at −80° C. in the corresponding medium containing 20% glycerol (w/v). Frozen stocks were activated by re-suspending 100 µl of each conserved strain in 10 ml of growth medium, followed by incubation for 18-24 h at the corresponding temperature.

Antimicrobial Activity of *Paenibacillus polymyxa* JB05-01-1 Culture Supernatant To demonstrate that inhibition of *E. coli* ATCC 25922 by *P. polymyxa* JB05-01-1 was attributed in part to secreted substances, culture supernatant was tested using a qualitative agar well diffusion method (Wolf and Gibbons, 1996). Briefly, TSBYE containing 0.75% (w/v) agar was cooled to 47° C., seeded with overnight culture of *E. coli* ATCC 25922 (1% vol), and poured into sterile Petri plates. Wells (7 mm) were cut in the solidified agar using a sterile metal cork borer and filled with 80 µl of *P. polymyxa* culture supernatant. The plates were incubated at 5° C. for 2 h to allow diffusion of the supernatant; the incubation continued aerobically for 18 h at 30° C. After this period, the plates were inspected for the presence or absence of zones of inhibition.

Antagonism Between *P. polymyxa* JR05-01-1 and *E. coli* ATCC 25922

*P. polymyxa* JB05-01-1 culture (10 ml) was centrifuged and the cells were re-suspended in 50 μl of LB broth. 20 μl of the suspension were deposited into a 5-mm paper disc. The paper discs impregnated with bacterial cell suspension were placed on the surface of TSBYE seeded with overnight culture of *E. coli* ATCC 25922 (0.25 ml in 25 ml), solidified with 0.75% agar and poured at 47° C. into Petri plates. The plates were incubated aerobically at 30° C. for 18 h and checked for zones of inhibition (clear agar) surrounding the paper discs (Lenni and Mauliya, 2010).

Tolerance of *P. polymyxa* JB05-01-1 to Lysozyme, Acid, Bile and Hydrogen Peroxide ($H_2O_2$)

Tolerance of the three *P. polymyxa* strains to lysozyme, acidic conditions, bile salts and hydrogen peroxide was tested using sterile flat-bottom 96-well microtiter plates (Falcon, Becton Dickinson and Company, Frankin Lakes, N.J., USA; Gagnon et al. 2004). Egg-white lysozyme (Sigma, 48,000 U/mg protein) was added at different concentrations (0, 3.9, 7.8, 15.6, 31.25, 62.5, 125, 250, 500, 1000 μg/ml) to TSBYE broth. The medium was adjusted to different pH values (7.0, 6.5, 6, 5.5, 5.0, 4.75, 4.5, 4.25, 4.0) using 1M HCl. For another purpose, bovine bile salts (Sigma) were added to the medium at different concentrations (0.1%, 0.2%, 0.3%, and 0.4% w/v). Similarly, to study the effect of $H_2O_2$, different concentrations (0, 2.5, 5, 10, 20 and 40 μg/ml) of $H_2O_2$ purchased from Merck (Darmstadt, Germany) was added. Wells (in duplicate) containing 200 μl of tested broth were inoculated with 20 μl of overnight culture of *P. polymyxa* diluted 1/100 in TSBYE. Microplates were incubated under anaerobic conditions at 30° C. for 18 h. Optical densities (OD) were read at 630 nm using a Thermomax microplate reader (Zeus, scientific Inc, Raritan, N.J.). Resistance to $H_2O_2$ and lysozyme (minimum inhibitory concentration) was expressed as the lowest concentration that maintained the OD under 50% of the OD in the "0" concentration wells. Acid resistance was expressed as the lowest pH at which the tested strain had an OD at least 40% of its level at pH 6.5.

Tolerance to Gastric Acidity

Determination of the tolerance to a simulated gastric transit was based on the procedure described by Charteris et al. (1998). A simulated gastric juice was prepared by suspending pepsin (3 mg/ml) in sterile saline (0.5% w/v) and adjusting the pH to 2.0 with concentrated HCl. Overnight 2 ml cultures of the three *P. polymyxa* variants were subjected to centrifugation in an Eppendorf centrifuge at 5000 g for 5 min and washed two times in quarter-strength Ringer's solution at pH 7. Then, 0.3 mL of the washed suspension was added to 1.5 mL of simulated gastric juice (pH 2.0) in a 2.0 mL Eppendorf tube and vortexed. In the controls, simulated gastric juice was replaced by 1.5 mL quarter-strength Ringer's solution and these samples were used for determination of the initial cell counts. Aliquots of 0.2 mL were removed after 15, 30, and 90 min at 37° C. and viable counts were determined by plating serial 10-fold dilutions on LB agar and counting the colony numbers after anaerobic incubation at 37° C. for 48 h. Experiments were carried out in duplicate and were repeated two times. Results are expressed as the mean and standard deviation of three determinations.

Carbohydrate Utilization

The abilities of *P. polymyxa* JB05-01-1 and other *P. polymyxa* strains (ATCC 43865, ATCC 7070) to utilize sugars, glycogen and pyruvate, to grow in the presence of 6.5% NaCl and finally to tolerate polymyxin B were determined using the Vitek 2 colorimetric GN-BCL card for the identification of Gram-positive spore-forming microorganisms of the family Bacillaceae (BioMerieux, Inc. Hazelwood, Mo., USA) according to the manufacturer's instructions (Scheldeman et al. 2004). Results were reported as negative or positive. The carbohydrate utilization profiles were compared and the homology was determined using the Vitek 2 compact system (BioMerieux, Inc. Hazelwood, Mo., USA).

Determination of Cell Affinity for Hydrocarbons

*P. polymyxa* JB05-01-1 and reference strains ATCC 43865 and ATCC 7070 were grown in TSBYE media at 30° C. to the logarithmic growth phase, harvested by centrifugation (3000 g, 10 min), washed twice, and resuspended at a concentration of $10^8$ CFU $ml^{-1}$ in 0.15 mol $l^{-1}$ NaCl solution. Hexadecane or decane (0.4 ml) was vortexed for 60 sec and the suspension was allowed to stand for 30 min (Doyle and Rosenberg, 1995). Absorbance by the aqueous phase at 400 nm was measured using a spectrophotometer (Molecular Devices Corp., Sunnyvale, Calif., USA). The percentage of cells extracted into each hydrocarbon liquid was determined by the following formula: $100 \times [1-(A/A_0)]$, where $A_0$ and A are absorbance by the aqueous phase prior to and after mixing.

Caco-2 Cell Culture and Bacterial Adhesion Assay

Enterocyte-like Caco-2 cells (ATCC HTB-37) obtained from the American Type Culture Collection (Rockville, Md.) were cultured routinely under a 5% (v/v) CO, atmosphere at 37° C. as monolayer in Dulbecco-modified Eagle's minimal essential medium (DMEM; Gibco) containing 25 mM glucose, 4 mM glutamine and 1 mM sodium pyruvate (Gagnon et al. 2004), and then in medium supplemented with 20% (v/v) fetal calf serum (Hyclone Laboratories, Logan, Utah, USA). Wells in Multiwell tissue culture plates (Falcon, Becton-Dickinson) were seeded each with $10^4$ cells. The culture medium was replaced every 48 h and confluent monolayers obtained after the tenth sub-culture was used for the adhesion assay. Trypan Blue was used for viable staining and cells were counted by hemocytometer (Hausser scientific, Horsham, Pa., USA).

The procedure of Cepeljnik et al. (2007) was followed. Caco-2 cell monolayers were washed twice with sterile phosphate-buffered saline (PBS, 100 mM, pH 7.3) and submerged in DMEM for 18 h, followed by one wash with PBS. Overnight culture of *P. polymyxa* in TSBYE broth was centrifuged and the bacterial cells were washed twice with PBS, suspended in DMEM at approximately $4 \times 10^4$ CFU/ml or $4 \times 10^6$ CFU/ml and 2 ml were added to the wells. Adhesion to Caco-2 cells was evaluated at 15, 30 and 60 min by washing twice with sterile PBS followed by addition of 0.25 ml of trypsin-EDTA (0.05% trypsin, 0.53 mM $Na_4$-EDTA; Gibco). After 15 min of incubation at 37° C., 0.25 ml of DMEM supplemented with 20% FCS was added to each well to stop the trypsin reaction and the Caco-2 layer was detached by pipetting. Serial 10-fold dilutions were then plated on *Bacillus cereus* agar (Difco Laboratories), followed by incubation under aerobic conditions for 24 h at 37° C.

Results

Antimicrobial Activity of *Paenibacillus polymyxa* JB05-01-1 Culture Supernatant The antimicrobial substance(s) produced by *P. polymyxa* JB0501 was confirmed qualitatively using the agar diffusion test (FIG. 7A) against *E. coli* ATCC 25922 as the indicator strain.

Antagonism Between *Paenibacillus polymyxa* JB05-01-1 and *E. coli* ATCC 25922

Using the spot test, *P. polymyxa* JB05-01-1 was found to be antagonistic towards *E. coli* ATCC 25922 (FIG. 7B). Paper discs loaded with *P. polymyxa* JB05-01-1 produced clear zones of inhibition about 8 mm in diameter. TSB medium was tested as negative control.

Lysozyme, Acid, Bile and Hydrogen Peroxide Tolerance by *Paenibacillus polymyxa* JB05-01-1

For a probiotic candidate, it must display the ability to survive under gastrointestinal tract conditions. This means to begin with, resistance to salivary lysozyme, gastric acid (HCl) and bile. The "candidate" should also be able to establish itself among the intestinal microbiota. The ability of *P. polymyxa* JB05-01-1 to grow in the presence of lysozyme, acidic pH, bile salts and $H_2O_2$ is shown in Table 5. *P. polymyxa* JB05-01-1 was able to grow in the presence of egg-white lysozyme concentrations up to 16.5 μg/ml which is supposed to be more than the physiological concentration of intestinal lysozyme (Suskovic et al. 1997). ATCC 43865 and ATCC 7070 isolates were able to tolerate higher concentrations of 31.25-62.5 μg/ml. All three strains of *P. polymyxa* grew at pH 4.75 or lower (Table 5). Indeed JB05-01-1 and ATCC 43865 were able to grow at a lower pH (4.5). Acidity is believed to be the most detrimental factor affecting the growth and viability of probiotic bacteria, growth being slowed down significantly below pH 4.5 (Lankaputhra et al. 1995). *P. polymyxa* JB05-01-1 should therefore survive in fermented products and perhaps contribute to prolonging product shelf life. No growth was observed for any of the strains in the presence of 0.2% bile salts. The maximum $H_2O_2$ concentration tolerated by *P. polymyxa* JB05-01-1 was between 7.3 to 14.6 μg/ml.

TABLE 5

Tolerance of gastrointestinal factors by *Paenibacillus polymyxa*

| | Substance | | | |
| --- | --- | --- | --- | --- |
| Variant or strain | Lysozyme (μg/ml)[1] | Acid (HCl)[2] | Bile salts (0.2%) | $H_2O_2$ (μg/ml)[1] |
| *P. polymyxa* JB05-01-1 | 16.25 | 4.5 | —[3] | 7.3-14.6 |
| *P. polymyxa* ATCC 43865 | 31.25-62.5 | 4.5 | — | 14.6 |
| *P. polymyxa* ATCC 7070 | 31.25-62.5 | 4.75 | — | 7.3-14.6 |

[1]Minimum inhibitory concentration (MIC)
[2]Minimum growth pH
[3]— No growth

Tolerance to Gastric Acidity and Cell Affinity for Hydrocarbons

Figure 9:
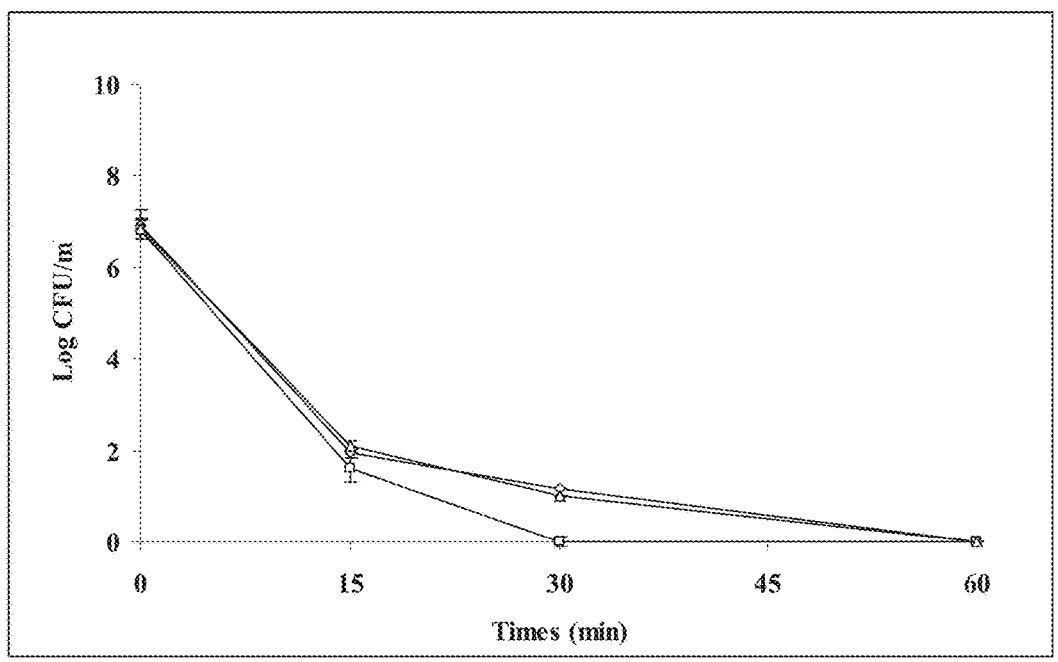
FIG. 9 shows the tolerance (Log CFU per ml) of selected *P. polymyxa* JB05-01-1 (♦), *P. polymyxa* ATCC 43865 (□) and *P. polymyxa* ATCC 7070 (Δ) strains to a simulated gastric juice (pH 2.0) over time (mins). Results are means of two independent experiments, vertical bars represent standard deviations.

Exposure of *P. polymyxa* JB05-01-1, *P. polymyxa* ATCC 43865 and *P. polymyxa* ATCC 7070 strains to a simulated gastric buffer containing pepsin at pH 2.0 resulted in a rapid loss of viability (FIG. 9). Viable counts of variant *P. polymyxa* JB05-01-1 strains decreased from about 6.93 to 1.61 Log CFU per ml within 15 min *P. polymyxa* JB05-01-1 displayed higher affinity for both hexadecane and decane than the *P. polymyxa* ATCC 43865 and *P. polymyxa* ATCC 7070 (FIG. 8).

Carbohydrate Utilization and Other Physiological Factors

Table 6 shows the carbohydrate utilization profiles, the tolerance of salt or polymyxin B, and the calculated homology based on these 14 traits for the three variants of *P. polymyxa*. Strain JB05-01-1 displayed a homology of approximately 98%, confirming the high probability that it does indeed belong to the genus *Paenibacillus*.

TABLE 6

Carbohydrate utilization profile, growth in 6.5% NaCl, polymyxin B resistance and homology of three strains of *Paenibacillus polymyxa*

| | Bacterial strain | | |
| --- | --- | --- | --- |
| Physiological test | JB05-01-1 | ATCC 43865 | ATCC 7070 |
| D-Galactose | + | + | + |
| Maltotriose | + | + | + |
| D-Mannose | + | + | + |
| D-Melezitose | + | − | − |
| D-Tagatose | − | − | − |
| D-Trehalose | + | + | + |
| Palatinose | + | + | + |
| L-Rhamnose | − | − | − |
| D-Glucose | + | + | + |
| d-Ribose | + | + | + |
| Glycogen | + | + | + |
| Pyruvate | − | + | + |
| Growth in 6.5% NaCl | − | + | + |
| Tolerance of polymyxin B | + | + | + |
| Homology (%) | 98 | 91 | 88 |

Adhesion of *Paenibacillus polymyxa* to Caco-2 Cells

The quantitative adhesion of *P. polymyxa* JB05-01-1 and *P. polymyxa* ATCC 43865 and ATCC 7070 to monolayers of enterocyte-like cells is depicted in Table 7. Starting from initial numbers of about $8.7 \times 10^6$ and $6.8 \times 10^6$ CFU/well, the number of adherent bacterial cells after 1 h of contact was about $3.4 \pm 0.16 \times 10^4$ CFU/well and $4.8 \pm 0.26 \times 10^4$ CFU/well respectively for *P. polymyxa* JB05-01-1 and *P. polymyxa* ATCC 43865. Starting from initial numbers 100 times smaller, the numbers of adherent bacterial cells were about ten times smaller. In both *P. polymyxa* JB05-01-1 and *P. polymyxa* ATCC 43865, adhesion ranged from about 0.35% to about 6.5% of the initial numbers contacted with the enterocytes; the proportion being decreased at the higher initial load suggesting that saturation of the adhesion sites was approached at the higher bacterial load tested. Contact time with the Caco-2 monolayer had little effect on the number of adherent bacterial cells counted.

TABLE 7

Adhesion of *Paenibacillus polymyxa* JB05-01-1, *Paenibacillus polymyxa* ATCC 43865 and *Paenibacillus polymyxa* ATCC 7070 to Caco-2 cells

| | Adherent bacteria (CFU/well)* | | | |
| --- | --- | --- | --- | --- |
| | Initial load | 15 min | 30 min | 60 min |
| *P. polymyxa* JB05-01-1 | $8.7 \pm 0.53 \times 10^6$ | $3.1 \pm 0.1 \times 10^4$ | $3.1 \pm 0.31 \times 10^4$ | $3.4 \pm 0.16 \times 10^4$ |
| | $8.7 \pm 0.45 \times 10^4$ | $5.3 \pm 0.22 \times 10^3$ | $4.4 \pm 0.68 \times 10^3$ | $4.8 \pm 0.42 \times 10^3$ |

TABLE 7-continued

Adhesion of *Paenibacillus polymyxa* JB05-01-1, *Paenibacillus polymyxa*
ATCC 43865 and *Paenibacillus polymyxa* ATCC 7070 to Caco-2 cells

| | Adherent bacteria (CFU/well)* | | | |
|---|---|---|---|---|
| | Initial load | 15 min | 30 min | 60 min |
| P. polymyxa ATCC 43865 | $6.8 \pm 0.45 \times 10^6$ $6.8 \pm 0.37 \times 10^4$ | $3.2 \pm 0.21 \times 10^4$ $4.4 \pm 0.33 \times 10^3$ | $2.8 \pm 0.53 \times 10^4$ $2.4 \pm 0.22 \times 10^3$ | $4.8 \pm 0.26 \times 10^4$ $3.7 \pm 0.32 \times 10^3$ |
| P. polymyxa ATCC 7070 | $7.1 \pm 0.65 \times 10^6$ $7.1 \pm 0.22 \times 10^4$ | $3.8 \pm 0.21 \times 10^4$ $2.4 \pm 0.33 \times 10^2$ | $3.3 \pm 0.13 \times 10^4$ $5.5 \pm 0.58 \times 10^2$ | $4.8 \pm 0.46 \times 10^4$ $4.1 \pm 0.51 \times 10^2$ |

*Mean ± S.E. of duplicate analyses

Example 8: Probiotic Effect on Growth Performance of Broiler Chickens

A preparation of JB05-01-1 supernatant (labeled P3) was produced as a dietary supplement for a field trial. A TSB medium with 0.4% yeast extract was prepared for a 1 liter fermentor which was in turn inoculated with the test culture. The culture was grown at 30° C. for 18 hours. The resulting culture was centrifuged at 12,000 g for 15 minutes at 4° C. The centrifuged cultures were then heated to between 80 and 100° C. in a water bath allowing the supernatant to be separated from the pellet. The supernatant was then stored at 4° C. for use in the trial. 500 day-old broiler chicks were divided into five treatment groups, each group containing 4 cohorts of 25 birds. The five different treatment groups of broiler chickens were given different amounts of dietary supplements for a four week period. The treatment regimes were as follows:

T1=Normal Diet (control)
T2=Normal Diet+1.5 ml RE3™ per kg feed
T3=Normal Diet+0.5 ml P3 per kg feed
T4=Normal Diet+1 ml P3 per kg feed
T5=Normal Diet=1.5 ml P3 per kg feed Results Summary of results at the end of week 4 are shown in Table 8.

TABLE 8

The effect of varying levels of P3 on the growth performance of broiler chickens

| | Dietary treatment | | | | |
|---|---|---|---|---|---|
| Parameter | T1 Control | T2 1.5 ml RE3/kg feed | T3 0.5 ml P3/kg feed | T4 1 ml P3/kg feed | T5 1.5 ml P3/kg feed |
| Initial weight/bird (g) | 47 | 47 | 47 | 47 | 47 |
| Final weight/bird (g) | 1041 | 1006 | 1058 | 1025 | 1036 |
| Feed intake/bird (g) | 1780 | 1673 | 1729 | 1711 | 1731 |
| Weight gain/bird (g) | 994 | 959 | 1011 | 978 | 989 |
| FCR (intake/gain) | 1.79 | 1.75 | 1.71 | 1.75 | 1.75 |
| Mortality (%) | 7 | 5 | 5 | 1 | 1 |

Addition of dietary supplements RE3 or P3 to chicken feed resulted in a slightly better feed conversion rate (FCR) of the feed than when no dietary supplement is added (control) indicating that addition of these dietary supplements results in a higher weight gain in chickens for equivalent feed intake. Provision of dietary supplements RE3 or P3 to feed also resulted in fewer mortalities, with supplement P3 added at levels of 1 ml or 1.5 ml per kg of feed having the lowest mortality rate.

Example 9: Genome Assembly and Annotation

The genome of *Paenibacillus polymyxa* JB05-01-1 ("JB05-01-1 genome") was sequenced by MiSeq Illumina sequencing (Eurofins MWG, Germany). The size of the genome was 5.9 Mb, with a 45.7% G/C content.

TABLE 9

Features of the assembled JB05-01-1 genome Contig/Scaffold Overview

Sample: P_PJB005

|  | All Contigs | Large Contigs | Scaffolds | Large Scaffolds |
|---|---|---|---|---|
| Total Entries: | 70 | 30 | 42 | 5 |
| Total Length: | 5 961 671 | 5 949 216 | 5 993 163 | 5 981 904 |
| Min Length: | 173 | 1 029 | 173 | 1 029 |
| Max Length: | 1 668 666 | 1 668 666 | 5 976 888 | 5 976 888 |
| Mean Length: | 85 266 | 198 307 | 142 694 | 1 196 380 |
| M50: | 5 12 780 | 5 12 780 | 5 976 888 | 5 976 888 |
| M90: | 173 980 | 173 980 | 1 561 | 1 561 |
| GC Content: | 45.7 | 45.7 | 45.7 | 45.7 |
| #A: | 1 618 632 | 1 615 645 | 1 618 632 | 1 615 858 |
| #T: | 1 630 418 | 1 616 533 | 1 619 418 | 1 616 700 |
| #G: | 1 358 605 | 1 365 323 | 1 358 075 | 1 365 642 |
| #C: | 1 364 926 | 1 361 715 | 1 364 926 | 1 362 143 |
| #N: | 0 | 0 | 31 492 | 31 492 |

Sample: P_PJB005

| Scaffold | Length | k-mer coverage |
|---|---|---|
| scf_77 | 5 976 888 | 30.694033 |
| scf_12 | 1 561 | 87.979660 |
| scf_10 | 1 292 | 133.200954 |
| scf_41 | 1 134 | 56.627861 |
| scf_7 | 1 029 | 373.688341 |

The JB05-01-1 genome consists of 70 contigs, ranging from 173 bp to 1 658 666 bp in size, assembled in 5 large scaffolds.

The JB05-01-1 genome sequence was compared with available sequenced genomes of five *Paenibacillus polymyxa* strains (E681, SC2, M1, CR1 et SQR21). The contigs were reordered based on the reference strain E681 with ACT and WebACT. The JB05-01-1 genome was annotated using the RAST server (automated annotation), which identified 5489 coding sequences and 127 RNAs.

TABLE 10

Overview of annotated JB05-01-1 genome: gene subsystems and functions

| Subsystems | Feature Count | Percentage % |
|---|---|---|
| Cofactors, Vitamins, Prosthetic Groups Pigments | 235 | 7.94 |
| Cell Wall and Capsule | 154 | 5.20 |
| Virulence, Disease, and Defense | 95 | 3.21 |
| Potassium metabolism | 9 | 0.30 |
| Photosynthesis | 0 | 0.0 |
| Miscellaneous | 24 | 0.81 |
| Phages, Prophages, Transposable elements, Plasmids | 16 | 0.54 |
| Membrane Transport | 92 | 3.11 |
| Iron acquisition and metabolism | 35 | 1.18 |
| RNA Metabolism | 161 | 5.44 |
| Nucleosides and Nucleotides | 115 | 3.88 |
| Protein Metabolism | 223 | 7.53 |
| Cell Division and Cell Cycle | 27 | 0.91 |
| Motility and Chemotaxis | 69 | 2.33 |
| Regulation and Cell signaling | 59 | 1.99 |
| Secondary Metabolism | 125 | 4.22 |
| Fatty acids, Lipids, and Isoprenoids | 131 | 4.42 |
| Nitrogen Metabolism | 31 | 1.05 |
| Dormancy and Sporulation | 97 | 3.28 |
| Respiration | 53 | 1.79 |
| Stress Response | 85 | 2.87 |
| Metabolism & Aromatic compounds | 7 | 0.24 |
| Amino Acids & derivatives | 344 | 11.62 |
| Sulfur Metabolism | 51 | 1.72 |
| Phosphorus Metabolism | 67 | 2.26 |
| Carbohydrates | 656 | 22.15 |
| Total | 2961 | 100.00 |

Features of Interest

The JB05-01-1 genome contains genes coding for several antibacterial peptides, for example, polymyxin synthesis gene cluster, bacitracin and fusaricidin synthetases. The JB05-01-1 genome also contains multiple antibiotic resistance genes. Genes coding for bacitracin synthetases (annotated as bacitracin synthetase 3 BA3) were identified as follows:

A 23727 bp synthetase (PEG 83, contig 43b 88285-112011), which is 97% identical to the *P. Polymyxa* E681 bacitracin synthetase 3

A 7767 bp synthetase (PEG 1749, contig 48 209298-217064), which shares 95% identity with the *P. polymyxa* M1 non-ribosomal peptide synthase NrsB A 12543 bp synthetase (PEG1750, contig 48 217075-229617), which is 92% identical to *P. polymyxa* M1 non-ribosomal peptide synthase NrsC A 4494 bp gene (PEG1962, contig 48, 460576-456083), which shares 99% identities with a gene annotated as a peptide synthetase in *P. polymyxa* CR1.

A 3870 bp gene (PEG1977, contig 48, 512190-516059).

Another gene of interest was found (PEG 3093, contig 52 6122-17335) coding for a 11214 bp Malonyl CoA-acyl carrier protein transacylase which shares 99% identity with the *P. polymyxa* CR1 fusaricidin synthetase gene.

TABLE 11

Primers sequences for the bacitracin and fusaricidin synthetases identified in the JB05-01-1 genome

| | Sequence (5' to 3') | Length (bp) | G/C content (%) | Tm (° C.) |
|---|---|---|---|---|
| PEG83_F | ATGAATGACATGCAG TTATA (SEQ ID NO: 2) | 20 | 30 | 44 |
| PEG83_R | TTAGGACAAAATGGG CTTGT (SEQ ID NO: 3) | 20 | 40 | 48 |
| PEG1749_F | ATGAGAAACGCACTC ATTCA (SEQ ID NO: 4) | 20 | 40 | 48 |
| PEG1749_R | CTAGGAAGATGTATT ATTTTTATAG (SEQ ID NO: 5) | 25 | 24 | 48 |
| PEG1750_F | ATGAGTAAAGATCTG CAAATTCA (SEQ ID NO: 6) | 23 | 31 | 48 |
| PEG1750_R | TTACAGAACCGCTGC CCAGC (SEQ ID NO: 7) | 20 | 60 | 56 |
| PEG1962_F | ATGTTCTATGCATTA ACGCAT (SEQ ID NO: 8) | 21 | 33 | 47 |
| PEG1962_R | TTATTCAAAAAGCAA ATCTTCAAT (SEQ ID NO: 9) | 24 | 21 | 45 |
| PEG1977_F | ATGCATTATGAAGGA TATGA (SEQ ID NO: 10) | 20 | 30 | 44 |
| PEG1977_R | TTACCTCAAAAATGT ATTCA (SEQ ID NO: 11) | 20 | 25 | 42 |
| PEG3093_F | TTGAAAGCCTTATTT GAGAAG (SEQ ID NO: 12) | 21 | 33 | 47 |
| PEG3093_R | TCAAGATTTATGATG TGCCA (SEQ ID NO: 13) | 20 | 35 | 46 |

The 2613 bp lantionine synthetase LanL (PEG 2150, contig 48 697422-700034) was also identified. In addition, two other genes coding for non-ribosomal peptide synthetases were identified: a 1407 bp gene (PEG1966, contig 48, 468244-469650: 1407 bp) and a 2025 bp gene (PEG1971, contig 48, 484672-486696).

The JB05-01-1 genome also contains a polymyxin synthesis gene cluster consisting of five genes, sharing high homology with the pmxABCDE genes (95-99% identities). The genes coding for PmxB, PmxC and PmxD located on contig 63 were identified as:

pmxB: PEG5404 (1899 bp, contig 63 10624-8726) annotated as a bacillibactin synthetase component F (97% identical to the pmxB gene in *Paenibacillus polymyxa* SQR-21)

pmxC: PEG5403 (1827 bp, contig 63 8736-6910) annotated as lipid A export ATP-binding/permease protein MsbA (96% identical to the pmxC gene in *P. polymyxa* M1 pmxD: PEG5402 (1734 bp, contig 63 6913-5180) annotated as lipid A export ATP-binding/permease protein MsbA (98% identical to the pmxD gene in *P. polymyxa* M1).

TABLE 12

Primer sequences for the polymyxin synthesis genes identified in the JB05-01-1 genome

| | Sequence (5' to 3') | Length (bp) | G/C content (%) | Tm (° C.) |
|---|---|---|---|---|
| PEG5402_F (6913) | TTGAAAAAGGGCGGATGGC TCTC (SEQ ID NO: 14) | 23 | 52 | 57 |
| PEG5402_R (5180) | CTAGCCGTACAGCCGGGC (SEQ ID NO: 15) | 18 | 72 | 57 |
| PEG5403_F (8736) | ATGGAAGCTGACCGGCAG (SEQ ID NO: 16) | 18 | 61 | 53 |
| PEG5403_R (6910) | TCAAGTGTACGCCACCTCC (SEQ ID NO: 17) | 19 | 58 | 53 |
| PEG5404_F (10624) | ATGTACGGAGCGCTGCTGT (SEQ ID NO: 18) | 19 | 58 | 53 |
| PEG5404_R (8726) | TCAGCTTCCATGCAGTACC (SEQ ID NO: 19) | 19 | 53 | 51 |

The pmxA and pmxE genes in the JB05-01-1 genome were not identified by automated annotation. The pmxA (15 030 bp) and the pmxE (18 940 bp) genes of *P. polymyxa* M1 were used as references to search the JB05-01-1 genome. Fragments of pmxA were found on contigs 62 (bases 1 to 1619), 60 (1796-2688), 66 (3132-5604), 67 (6075-8553) and 68 (9252-13125, 13659-15033). The pmxE gene appeared to be located on contigs 63 and 61.

REFERENCES

Andersson, A., Granumb, P. E., Ronnera, U. (1998). The adhesion of *Bacillus cereus* spores to epithelial cells might be an additional virulence mechanism International Journal of Food Microbiology 39, 93-99.

Altschul S F, Gish W, Miller W, Myers E W, Lipman D J. Basic local alignment search tool. J Mol Biol 1990; 215:403-410.

Angioi, A., Zanetyi, S., Sanna, A., Delogu, G., Fadda, G. (1995) Adhesiveness of *Bacillus subtilis* Strains to Epithelial Cells Cultured in vitro. Microbial Ecology in Health and Disease. 8: 71-77

Bhunia A K, Johnson M C, Ray, B. Direct detection of an antibacterial peptide of *Pediococcus acidilactici* in sodium dodecyl sulfate-polyacrylamide gel electrophoresis. J Ind Microbiol 1987; 2:319-322.

Caldwell D R, Bryant M P. Medium without rumen fluid for non selective enumeration and isolation of rumen bacteria. Appl Microbiol 1966; 14:794-801.

Cepeljnik, T., Lah, B., Narat, M., Marinsek-Logar, R. (2007) Adaptation of adhesion test using Caco-2 cells for anaerobic bacterium *Pseudobutyrivibrio xylanivorans*, a probiotic candidate. Folia Microbiol (Praha). 52:367-73.

Charteris, W. P., Kelly, P. M., Morelli, L., and Collins, J. K. (1998). Development and application of an in vitro methodology to determine the transit tolerance of potentially probiotic *Lactobacillus* and *Bifidobacterium* species in the upper human gastrointestinal tract. Journal of Applied Microbiology, 84, 759-768.

Cleveland J, Montville T J, Nes I F, Chikindas M L. Bacteriocins: Safe, natural antibacterials for food preservation. Int. J. Food Microbiol, 2001; 71:11-20.

Daba H, Lacroix C, Huang J, Simard R E, Lemieux L. Simple method of purification and sequencing of a bacteriocin produced by *Pediococcus acidilactici* UL5. J Appl Bacteriol 1994; 77:682-688.

Davies E A, Bevis H E, Potter R, Harris J, Williams G C, Delves-Broughton J. The effect of pH on the stability of nisin solution during autoclaving. Lett Appl Microbiol 1998; 27:186-187.

de Man J C, Rogosa M, Sharpe M E. A medium for the cultivation of lactobacilli. J Appl Bacteriol 1960; 23:130-135.

DeCrescenzo H E, Phillips D R, Doran Peterson J B. Polymyxin E production by *P. amylolyticus*. Letters Appl Microbiol 2007; 45:491-496.

Doyle, R. J., Nedjat-Haiem F. Singh J. S. (1984). Hydrophobic characteristics of *Bacillus* spores. Current Microbiology. 10: 329-333.

Doyle, R. J., Rosenberg, M. (1995). Measurement of microbial adhesion to hydrophobic substrata. Methods in Enzymology, 253, 542-550.

Du L, Shen B. Identification and characterization of a type II peptidyl carrier protein from the bleomycin producer *Streptomyces verticillus* ATCC 15003. Chem Biol. 1999; 6:507-517.

Falagas M E, and Kasiakou S K (2005). Colistin: the revival of polymyxins for the management of multidrug-resistant gram-negative bacterial infections. Clin Infect Dis. 40:1333-1341.

Falagas M E, Kasiakou S J (2006) Toxicity of polymyxins: a systematic review of the evidence from old and recent studies. Crit Care. 10:R27.

Fangio M F, Roura S I, Fritz R (2010) Isolation and identification of *Bacillus* spp. and related genera from different starchy foods. J Food Sci. 75:218-221.

Gagnon, M., Kheadr, E., Le Blay G., Fliss, I. (2004) vitro inhibition of *Escherichia coli* O157:H7 by bifidobacterial strains of human origin. International Journal of Food Microbiology 92, 69-78.

Govaerts C, Orwa J, Van Schepdael A, Roets E, Hoogmartens J (2002) Characterization of polypeptide antibiotics of the polymyxin series by liquid chromatography electrospray ionization ion trap tandem mass spectrometry. J. Pept. Sci. 8:45-55.

He Z, Kisla D, Zhang L, Yuan C, Green-Church K B, Yousef A E (2007) Isolation and identification of a *Paenibacillus polymyxa* strain that coproduces a novel lantibiotic and polymyxin. Appl Env Microbiol. 73:168-178.

He Z, Yuan C, Zhang L, Yousef A E (2008) N-terminal acetylation in paenibacillin, a novel lantibiotic. FEBS Lett. 582:2787-2792.

Jian Li, Milnel R W, Nation R L, Turnidge J D, Smeaton T C, Coulthard K (2004) Pharmacokinetics of colistin methanesulphonate and colistin in rats following an intravenous dose of colistin methanesulphonate J Antimicrobiol Chemother. 53: 837-840.

Kane M D, Poulsen L K, Stahl D A. Monitoring the enrichment and isolation of sulfate-reducing bacteria by using oligonucleotide hybridization probes designed from environmentally derived 16S rRNA sequences. Appl Environ Microbiol 1993; 59:682-686.

Kheadr E, Bernoussi N, Lacroix C, Fliss I. Comparison of the sensitivity of commercial strains and infant isolates of bifidobacteria to antibiotics and bacteriocins, Int Dairy J 2004; 14; 273-285.

Klaenhammer T R. Genetics of bacteriocins produced by lactic bacteria. FEMS Microbiol Rev 1993; 12:39-86.

Komura S, Kurahashi K. Biosynthesis of polymyxin E by a cell-free enzyme system. J Biochem 1985; 97:1409-1417.

Koshikawa, T., Yamazaki, M., Yoshimi, M., Ogawa, S., Yamada, A., Watabe, K., Tori, A., (1989) Surface Hydrophobicity of Spores of *Bacillus* spp. Journal of General Microbiology 135, 2717-2722.

Lampis G, Deidda D, Maullu C, Madeddu M A, Pompei R, Delle Monachie F, Satta G (1995) Sattabacins and sattazolins: new biologically active compounds with antiviral properties extracted from a *Bacillus* sp. J Antibiot (Tokyo). 48:967-72.

Landman D, Georgescu C, Martin D A, Quale J (2008) Polymyxins Revisited Clinical. Microbiol Rev. 21, 449-465.

Lankaputhra, E. V., Shah, N. P., 1995. Survival of *Lactobacillus acidophilus* and *Bifidobacterium* spp. in the presence of acid and bile salts. Cult. Dairy Prod. J. 30, 2-7.

Lenni Fitri and Betty Mauliya Bustam (2010) Screening of antimicrobial producing strains isolated from the soil of grassland rhizosphere in Pocut Meurah Intan Forest Park, Seulawah, Aceh Besar Biodiversitas, 11 129-132.

Lim L M, Ly N, Anderson D, Yang J C, Macander L, Jarkowski A 3rd, Forrest A, Bulitta J B, Tsuji B T (2010) Resurgence of colistin: a review of resistance, toxicity, pharmacodynamics, and dosing. Pharmacotherapy. 30:1279-91.

Liu W T, Marsh T L, Cheng H, Forney U. Characterization of microbial diversity by determining terminal restriction fragment length polymorphisms of genes encoding 16S rRNA. Appl Environ Microbiol 1997; 63:4516-4522.

Lowry O H, Rosebrough N J, Farr A L, Randall R J. Protein measurement with the Folin phenol reagent. J Biol Chem 1951; 193:267-275.

Marahiel M A, Stachelhaus T, Mootz H D. Modular peptide synthetases involved in nonribosomal peptide synthesis. Chem Rev 1997; 97:2651-2673.

Martin N I, Hu H, Moake M M, Churey J J, Whittal R, Worobo R W, Vederas J C. Isolation, structural characterization, and properties of mattacin (polymyxin M), a cyclic peptide antibiotic produced by *Paenibacillus kobensis* M. J Biol. Chem 2003; 278:13124-13132.

Motta A S, Lorenzini D M, Brandelli A. Purification and partial characterization of an antibacterial peptide produced by a novel *Bacillus* sp. Isolated from the amazon basin. Curr Microbiol 2007; 54:282-286.

Naghmouchi K, Drider D, Baah J, Teather R (2010) Nisin A and Polymyxin B as Synergistic Inhibitors of Gram-positive and Gram-negative Bacteria. Prob Ant Prot. 2: 98-103.

Naghmouchi K, Drider D, Fliss I. Action of divergicin M35, a class IIa bacteriocin, on liposomes and *Listeria*. J Appl Microbiol. 2007; 102:1508-17.

Naghmouchi K, Drider D, Hammami R, Hiss I. (2008) Effect of Antimicrobial Peptides Divergicin M35 and Nisin A on *Listeria monocytogenes* LSD530 Potassium Channels. Current Microbiol 56:609-612.

Nathaniel I M, Hu H, Moake M M, Churey J J, Whittal R, Worobo R W, and Vederas J C (2003) Isolation, Structural Characterization, and Properties of Mattacin (Polymyxin M), a Cyclic Peptide Antibiotic Produced by *Paenibacillus kobensis* M. J Biol Chem. 278: 13124-13132.

Nes J F, Diep D B, Havarstein L S, Bruberg M B, Eij sink V G, Holo H. Biosynthesis of bacteriocins in lactic acid bacteria. Antonie Leeuwenhock 1996; 70:113-128.

Scheldeman, P. Goossens, K., Rodriguez-Diaz, M, Pil, A., Goris, J., Herman, L., De Vos, P., Logan, N A., Heyndrickx M (2004). *Paenibacillus lactis* sp. nov., isolated from raw and heat-treated milk. International journal of systematic and evolutionary microbiology 54, 885-891.

Selim S, Negrel J, Govaerts C, Gianinazzi S, van Tuinen D (2005) Isolation and Partial Characterization of Antagonistic Peptides Produced by *Paenibacillus* sp. Strain B2 Isolated from the Sorghum Mycorrhizosphere. Appl Environ Microbiol. 71: 501-6507.

Suskovic, J., Brkic, B., Matosic, S., Maric, V., 1997. *Lactobacillus acidophilus* M92 as potential probiotic strain. Milchwissenschaft 52, 430-435.

Svetoch E A, Stern N J, Eruslanov B V, Kovalev Y N, Volodina L I, Perelygin V V, Mitsevich E V, Mitsevich I P, Pokhilenko V D, Borzenkov V N, Levchuk V P, Svetoch O E, Kudriavtseva T Y. Isolation of *Bacillus circulans* and *Paenibacillus polymyxa* strains inhibitory to *Campylobacter jejuni* and characterization of associated bacteriocins. J Food Prot 2005; 68:11-17.

Tagg J R, Dajani A S, Wannamaker L W. Bacteriocins of gram-positive bacteria Bacteriol Rev 1976; 40:722-56.

Wolf C E, Gibbons W R. Improved method for quantification of the bacteriocin nisin. J Appl Bacteriol 1996; 80:453-457.

Zengguo He, Kisla D, Zhang L, Yuan C, Green-Church K B, Yousef A. E. Isolation and identification of a *Paenibacillus polymyxa* strain that coproduces a novel lantibiotic and polymyxin. Appl Environ Microbiol 2007; 73:168-178.

Zheng G. Yan L Z, Vederas J C, Zuber P. Genes of the sbo-alb locus of *Bacillus subtilis* are required for production of the antilisterial bacteriocin subtilosin. J Bacteriol 1999; 181:7346-355.

Other Embodiments

The present invention has been described with regard to one or more embodiments. However, it will be apparent to persons skilled in the art that a number of variations and modifications can be made without departing from the scope of the invention as defined in the claims. Accordingly, although various embodiments of the invention are disclosed herein, many adaptations and modifications may be made within the spirit and scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range, and of sub-ranges encompassed therein. As used herein, the terms "comprising", "comprises", "having" or "has" are used as an open-ended terms, substantially equivalent to the phrase "including, but not limited to". Terms such as "the," "a," and "an" are to be construed as indicating either the singular or plural. Citation of references herein shall not be construed as an admission that such references are prior art to the present invention. All publications are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A method of reducing mortality in poultry comprising administering to the poultry an effective amount of a dietary supplement comprising a cell culture supernatant obtained from culturing:
   (a) an isolated *Paenibacillus polymyxa* bacterium which has a 16S ribosomal RNA (16SrRNA) gene containing a DNA comprising the base sequence of SEQ ID NO: 1; or
   (b) an isolated *Paenibacillus polymyxa* bacterium deposited at the ATCC® under the terms of the Budapest Treaty and designated Accession Number PTA-10436, said cell culture supernatant comprising at least one antimicrobial compound produced by (a) or (b) that inhibits growth of a Gram-negative staining bacterium, wherein the compound is selected from the group consisting of a compound with a molecular weight of about 1169 Da which includes a fatty acid moiety 6-methyloctanoyl, and a compound with a molecular weight of about 1155 Da which includes a fatty acid moiety 6-methylhepatanoyl, wherein at least 0.5 ml of the dietary supplement is added per kg of chicken feed and mortality is reduced in poultry receiving the chicken feed with the added dietary supplement relative to control poultry who receive the chicken feed without the dietary supplement.

2. The method of claim 1, wherein the *Paenibacillus polymyxa* bacterium genome comprises genes encoding antibacterial peptides selected from the group consisting of one or more polymyxin synthesis genes, one or more bacitracin synthetase genes, and one or more fusaricidin synthetase genes.

3. The method of claim 1, wherein the isolated *Paenibacillus polymyxa* bacterium is cultured in a culture medium comprising components selected from the group consisting of a carbon/energy source, a nitrogen source and biotin.

4. The method of claim 1, wherein the isolated *Paenibacillus polymyxa* bacterium is cultured in a culture medium comprising Luria-Bertani (LB) medium.

5. The method of claim 1, wherein the isolated *Paenibacillus polymyxa* bacterium is cultured in a culture medium comprising Tryptic soy broth (TSB) medium.

6. The method of claim 1, wherein the compound having a molecular weight of about 1169 Da is a colistin A and the compound having a molecular weight of about 1155 Da is a colistin B.

7. The method of claim 1, wherein the Gram-negative staining bacterium is selected from the group consisting of *Escherichia* sp., *Pantoea* sp., *Pseudomonas* sp., *Butyrivibrio* sp., *Fibrobacter* sp., *Salmonella* sp., *Shigella* sp., *Helicobacter* sp., and *Campylobacter* sp.

8. The method of claim 1, wherein the Gram-negative staining bacterium is selected from the group consisting of *Escherichia coli* RR1, *Escherichia coli* TB1, *Escherichia coli* O157:H7, *Pantoea agglomerans* BC1, *Pseudomonas fluorescens* R73, *Butyrivibrio fibrisolvens* OR85, *Fibrobacter succinogenes* and *Pseudomonas aeruginosa*.

9. The method of claim 1, wherein the anti-microbial compound does not inhibit the growth of a Gram-positive staining bacterium.

\* \* \* \* \*

UNITED STATES PATENT AND TRADEMARK OFFICE
CERTIFICATE OF CORRECTION

PATENT NO. : 9,809,865 B2
APPLICATION NO. : 14/642158
DATED : November 7, 2017
INVENTOR(S) : Ronald Teather et al.

It is certified that error appears in the above-identified patent and that said Letters Patent is hereby corrected as shown below:

In the Specification

Column 35, please replace Table 9 with the following table:

| Features of the assembled JB05-01-1 genome Contig/Scaffold Overview |||||
|---|---|---|---|---|
| Sample: PpJB005 |||||
|  | All Contigs | Large Contigs | Scaffolds | Large Scaffolds |
| Total Entries: | 70 | 30 | 42 | 5 |
| Total Length: | 5961671 | 5949216 | 5993163 | 5981904 |
| Min Length: | 173 | 1029 | 173 | 1029 |
| Max Length: | 1668666 | 1668666 | 5976888 | 5976888 |
| Mean Length: | 85166 | 198307 | 142694 | 1196380 |
| N50: | 512780 | 512780 | 5976888 | 5976888 |
| N90: | 173989 | 173989 | 1561 | 1561 |
| GC Content: | 45.7 | 45.7 | 45.7 | 45.7 |
| #A: | 1618632 | 1615645 | 1618632 | 1615858 |
| #T: | 1619418 | 1616533 | 1619418 | 1616700 |
| #G: | 1358695 | 1355323 | 1358695 | 1355642 |
| #C: | 1364926 | 1361715 | 1364926 | 1362143 |
| #N: | 0 | 0 | 31492 | 31492 |
| Sample: PpJB005 ||||
| Scaffold | Length || k-mer coverage |
| scf_77 | 5976888 || 30.694033 |
| scf_12 | 1561 || 87.979660 |
| scf_10 | 1292 || 133.208954 |
| scf_41 | 1134 || 56.627861 |
| scf_7 | 1029 || 373.888641 |

Signed and Sealed this
First Day of May, 2018

Andrei Iancu
*Director of the United States Patent and Trademark Office*